United States Patent
Zahniser et al.

(10) Patent No.: US 8,964,171 B2
(45) Date of Patent: *Feb. 24, 2015

(54) IDENTIFYING AND MEASURING RETICULOCYTES

(75) Inventors: Michael Zahniser, Jamaica Plan, MA (US); Russell Zahniser, Dorchester, MA (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/549,211

(22) Filed: Jul. 13, 2012

(65) Prior Publication Data

US 2013/0023007 A1    Jan. 24, 2013

Related U.S. Application Data

(60) Provisional application No. 61/510,614, filed on Jul. 22, 2011, provisional application No. 61/510,710, filed on Jul. 22, 2011.

(51) Int. Cl.
| | | |
|---|---|---|
| G01N 33/48 | (2006.01) | |
| G06K 9/00 | (2006.01) | |
| A61B 5/00 | (2006.01) | |
| G01N 15/14 | (2006.01) | |
| G06T 7/00 | (2006.01) | |
| G06T 7/60 | (2006.01) | |
| G01N 15/00 | (2006.01) | |

(52) U.S. Cl.
CPC .......... G01N 15/1475 (2013.01); G06T 7/0012 (2013.01); G06K 9/0014 (2013.01); G06T 7/602 (2013.01); *G01N 15/1429* (2013.01); *G01N 2015/0076* (2013.01); *G01N 2015/1472* (2013.01); *G06T 2207/10024* (2013.01); *G06T 2207/30024* (2013.01); *G06T 2207/30242* (2013.01)
USPC .............. 356/39; 382/133; 382/134; 600/322

(58) Field of Classification Search
None
See application file for complete search history.

(56) References Cited

U.S. PATENT DOCUMENTS

| | | | |
|---|---|---|---|
| 6,350,613 B1 | 2/2002 | Wardlaw et al. | |
| 6,955,872 B2 | 10/2005 | Maples et al. | |
| 7,903,241 B2 | 3/2011 | Wardlaw et al. | |
| 7,929,121 B2 * | 4/2011 | Wardlaw et al. | ................. 356/39 |
| 7,929,122 B2 | 4/2011 | Wardlaw et al. | |
| 2003/0030783 A1 | 2/2003 | Roche et al. | |
| 2006/0050947 A1 | 3/2006 | Petrou et al. | |
| 2007/0172956 A1 | 7/2007 | Magari et al. | |
| 2008/0199947 A1 | 8/2008 | Linssen et al. | |
| 2009/0041329 A1 | 2/2009 | Nordell et al. | |
| 2009/0238437 A1 | 9/2009 | Levine et al. | |
| 2009/0238438 A1 | 9/2009 | Wardlaw et al. | |
| 2009/0262993 A1 | 10/2009 | Kotsianti et al. | |
| 2009/0269799 A1 * | 10/2009 | Winkelman et al. | ............ 435/29 |
| 2010/0150443 A1 | 6/2010 | Zahniser | |
| 2011/0149061 A1 | 6/2011 | Wardlaw et al. | |

FOREIGN PATENT DOCUMENTS

| | | |
|---|---|---|
| EP | 0 548 983 | 6/1993 |
| WO | 02/079749 | 10/2002 |
| WO | WO 2008140969 A1 * | 11/2008 |

OTHER PUBLICATIONS

International Search Report & Written Opinion, Patent Cooperation Treaty, PCT Application No. PCT/US2012/033636, mailed Jul. 9, 2012; 10 pages.

International Search Report in PCT Patent Application No. PCT/US2012/033636, mailed on Jul. 9, 2012, 3 pgs.

International Preliminary Report on Patentability in PCT Patent Application No. PCT/US2012/033636, mailed on Oct. 24, 2013, 8 pgs.

International Search Report and Written Opinion issued in application No. PCT/US2012/046787, dated Oct. 31, 2012, 12 total pages.

* cited by examiner

*Primary Examiner* — Lisa J Hobbs
(74) *Attorney, Agent, or Firm* — Fish & Richardson P.C.

(57) ABSTRACT

Methods and systems for identifying reticulocytes in a blood sample deposited on a substrate include: illuminating the sample with incident light at two different wavelengths, obtaining a two-dimensional image of the sample corresponding to a first one of the wavelengths, and obtaining a two-dimensional image of the sample corresponding to a second one of the wavelengths; analyzing the images to identify a set of representative red blood cells; determining an area of each of the red blood cells in the set; determining a color value of each of the red blood cells in the set; and, for each one of the red blood cells in the set, identifying the red blood cell as a reticulocyte if the area of the red blood cell exceeds an area cutoff value and the color value of the red blood cell is less than a color cutoff value.

42 Claims, 5 Drawing Sheets

IDENTIFYING AND MEASURING RETICULOCYTES

CROSS-REFERENCE TO RELATED APPLICATIONS

This application claims priority under 35 U.S.C. §119(e) to the following U.S. Provisional Patent Applications: 61/510,614, filed on Jul. 22, 2011; and 61/510,710, filed on Jul. 22, 2011. The entire contents of each of the foregoing applications are incorporated by reference herein.

TECHNICAL FIELD

This disclosure relates to identifying, counting and measuring properties of reticulocytes in biological samples including blood and quality control compositions designed to mimic blood.

BACKGROUND

Reticulocytes are immature red blood cells typically characterized by elevated levels of RNA as compared to mature red blood cells. A reticulocyte count performed on a blood sample can provide important information about how quickly a patient's bone marrow is producing red blood cells. Thus, the quantity of reticulocytes in a patient's blood serves as an important diagnostic indicator, and is typically one parameter of a complete blood count. For example, a high recticulocyte count can signify possible internal trauma, blood loss, or certain types of anemia. A low reticulocyte count can signify certain dietary deficiencies (e.g., insufficient iron) or an illness affecting the bone marrow such as cancer. Disclosed herein are methods and systems for automated measurement of cell samples, including the identification, quantitation, and constituent measurement of reticulocytes in biological samples including blood and quality control compositions designed to mimic blood.

SUMMARY

The methods and systems disclosed herein permit automated identification and quantitation of reticulocytes in blood samples using spectroscopic imaging. This identification and quantitation is based on images of one or more cells, which images are acquired at different optical wavelengths. In particular, the methods and systems disclosed can be used to identify and measure properties of reticulocytes in a blood sample extracted from a patient. The properties can include a variety of parameters related to the shape and appearance of the reticulocytes, including area, perimeter, circularity, optical density, and spectral properties at different wavelengths. The reticulocytes can be selectively displayed to a technician (e.g., highlighted to distinguish them from mature red blood cells). Diagnostic information acquired from reticulocytes can also be displayed to the technician for further consideration (e.g., to determine conditions the patient may be suffering, and to select appropriate courses of therapy) and/or can be communicated to other automated devices, stored in electronic patient records, and transmitted to other health care professionals.

In general, in a first aspect, the disclosure features methods for identifying reticulocytes in a blood sample deposited on a substrate, the methods including: illuminating the sample with incident light at two different wavelengths, obtaining a two-dimensional image of the sample corresponding to a first one of the wavelengths, and obtaining a two-dimensional image of the sample corresponding to a second one of the wavelengths; analyzing the images to identify a set of representative red blood cells; determining an area of each of the red blood cells in the set; determining a color value of each of the red blood cells in the set; and for each one of the red blood cells in the set, identifying the red blood cell as a reticulocyte if the area of the red blood cell exceeds an area cutoff value and the color value of the red blood cell is less than a color cutoff value, where the color value of each one of the red blood cells includes a difference between optical density values of the red blood cell at the two illumination wavelengths.

Embodiments of the methods can include any one or more of the features disclosed herein.

One of the wavelengths can be between 400 nm and 475 nm, and the other wavelength can be between 575 nm and 600 nm.

Determining the color value of each of the identified red blood cells can include, for each one of the red blood cells: determining a set of pixels associated with the cell; determining optical densities corresponding to the first wavelength for each one of the set of pixels; determining optical densities corresponding to the second wavelength for each one of the set of pixels; determining a mean optical density corresponding to the first wavelength for the set of pixels; determining a mean optical density corresponding to the second wavelength for the set of pixels; and calculating a difference between the mean optical densities to determine the color value of the cell.

Determining the area of each of the red blood cells in the set can include, for each one of the red blood cells, determining a set of pixels associated with the cell, and determining the area of the cell by counting the number of pixels in the set. Determining the area of each of the red blood cells in the set can include, for each one of the red blood cells, determining a set of pixels associated with the cell, determining a polygon that circumscribes the set of pixels, and determining the area of the cell by calculating an area of the polygon.

The color cutoff value can be based on a percentile of a distribution of the color values of the red blood cells. The percentile can correspond to a 70th percentile within the distribution of color values of the red blood cells. The color cutoff value can correspond to a sum of the percentile and a color offset value. The methods can include determining the percentile and the color offset value based on a set of training data in which the numbers of reticulocytes are known. The area cutoff value can be based on a percentile of a distribution of the areas of the red blood cells. The percentile can correspond to a 20th percentile of the distribution of areas of the red blood cells. The area cutoff value can correspond to a sum of the percentile and an area offset value. The methods can include determining the percentile and the area offset value based on a set of training data in which the numbers of reticulocytes are known.

The methods can include excluding the red blood cell from the representative set if a standard deviation of optical densities of pixels associated with the red blood cell at one of the two wavelengths is larger than a cutoff value. The methods can include excluding the red blood cell from the representative set if a standard deviation of optical densities of pixels associated with the red blood cell at a wavelength different from the two wavelengths is larger than a cutoff value.

The methods can include, for each of the red blood cells identified as reticulocytes, determining a volume of the reticulocyte. The methods can include determining the volume of the reticulocyte based on integrated optical densities of the reticulocyte corresponding to multiple illumination wavelengths. The methods can include determining a mean reticulocyte volume parameter for the sample.

The methods can include, for each of the red blood cells identified as reticulocytes, determining a hemoglobin content of the reticulocyte. The methods can include determining the hemoglobin content of the reticulocyte based on a weighted combination of an area of the reticulocyte, volumes of the reticulocyte corresponding to multiple illumination wavelengths, and integrated optical densities of the reticulocyte corresponding to the multiple illumination wavelengths. The methods can include determining a mean reticulocyte hemoglobin value for the sample.

Embodiments of the methods can also include any of the other features and steps disclosed herein, in any combination, as appropriate.

In another aspect, the disclosure features systems for identifying reticulocytes in a blood sample deposited on a substrate, the systems including a source configured to illuminate the sample with incident light at two different wavelengths, a detector configured to obtain a two-dimensional image of the sample corresponding to a first one of the wavelengths and to obtain a two-dimensional image of the sample corresponding to a second one of the wavelengths, and an electronic processor configured to: analyze the images to identify a set of representative red blood cells; determine an area of each of the red blood cells in the set; determine a color value of each of the red blood cells in the set; and for each one of the red blood cells in the set, identify the red blood cell as a reticulocyte if the area of the red blood cell exceeds an area cutoff value and the color value of the red blood cell is less than a color cutoff value, where the electronic processor is configured to determine the color value of each one of the red blood cells based on a difference between optical density values of the red blood cell at the two illumination wavelengths.

Embodiments of the systems can include any one or more of the following features.

The first wavelength can be between 400 nm and 475 nm, and the second wavelength can be between 575 nm and 600 nm.

For each one of the red blood cells in the set, the electronic processor can be configured to determine the color value of the cell by: determining a set of pixels associated with the cell; determining optical densities corresponding to the first wavelength for each one of the set of pixels; determining optical densities corresponding to the second wavelength for each one of the set of pixels; determining a mean optical density corresponding to the first wavelength for the set of pixels; determining a mean optical density corresponding to the second wavelength for the set of pixels; and calculating a difference between the mean optical densities to determine the color value of the cell.

For each one of the red blood cells in the set, the electronic processor can be configured to determine the area of the cell by determining a set of pixels associated with the cell, and determining the area of the cell by counting the number of pixels in the set. For each one of the red blood cells, the electronic processor can be configured to determine the area of the cell by determining a set of pixels associated with the cell, determining a polygon that circumscribes the set of pixels, and determining the area of the cell by calculating an area of the polygon.

The electronic processor can be configured to determine the color cutoff value based on a percentile of a distribution of the color values of the red blood cells. The percentile can correspond to a 70th percentile within the distribution of color values of the red blood cells. The electronic processor can be configured to determine the color cutoff value as a sum of the percentile and a color offset value. The electronic processor can be configured to determine the percentile and the color offset value based on a set of training data in which the numbers of reticulocytes are known. The electronic processor can be configured to determine the area cutoff value based on a percentile of a distribution of the areas of the red blood cells. The percentile can correspond to a 20th percentile of the distribution of areas of the red blood cells. The electronic processor can be configured to determine the area cutoff value as a sum of the percentile and an area offset value. The electronic processor can be configured to determine the percentile and the area offset value based on a set of training data in which the numbers of reticulocytes are known.

The electronic processor can be configured to exclude the red blood cell from the representative set if a standard deviation of optical densities of pixels associated with the red blood cell at one of the two wavelengths is larger than a cutoff value. The electronic processor can be configured to exclude the red blood cell from the representative set if a standard deviation of optical densities of pixels associated with the red blood cell at a wavelength different from the two wavelengths is larger than a cutoff value.

For each of the red blood cells identified as reticulocytes, the electronic processor can be configured to determine a volume of the reticulocyte. The electronic processor can be configured to determine the volume of the reticulocyte based on integrated optical densities of the reticulocyte corresponding to multiple illumination wavelengths. The electronic processor can be configured to determine a mean reticulocyte volume parameter for the sample.

For each of the red blood cells identified as reticulocytes, the electronic processor can be configured to determine a hemoglobin content of the reticulocyte. The electronic processor can be configured to determine the hemoglobin content of the reticulocyte based on a weighted combination of an area of the reticulocyte, volumes of the reticulocyte corresponding to multiple illumination wavelengths, and integrated optical densities of the reticulocyte corresponding to the multiple illumination wavelengths. The electronic processor can be configured to determine a mean reticulocyte hemoglobin value for the sample.

Embodiments of the systems can also include any of the other features disclosed herein, in any combination, as appropriate.

Unless otherwise defined, all technical and scientific terms used herein have the same meaning as commonly understood by one of ordinary skill in the art to which this disclosure belongs. Although methods and materials similar or equivalent to those described herein can be used in practice or testing, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1:
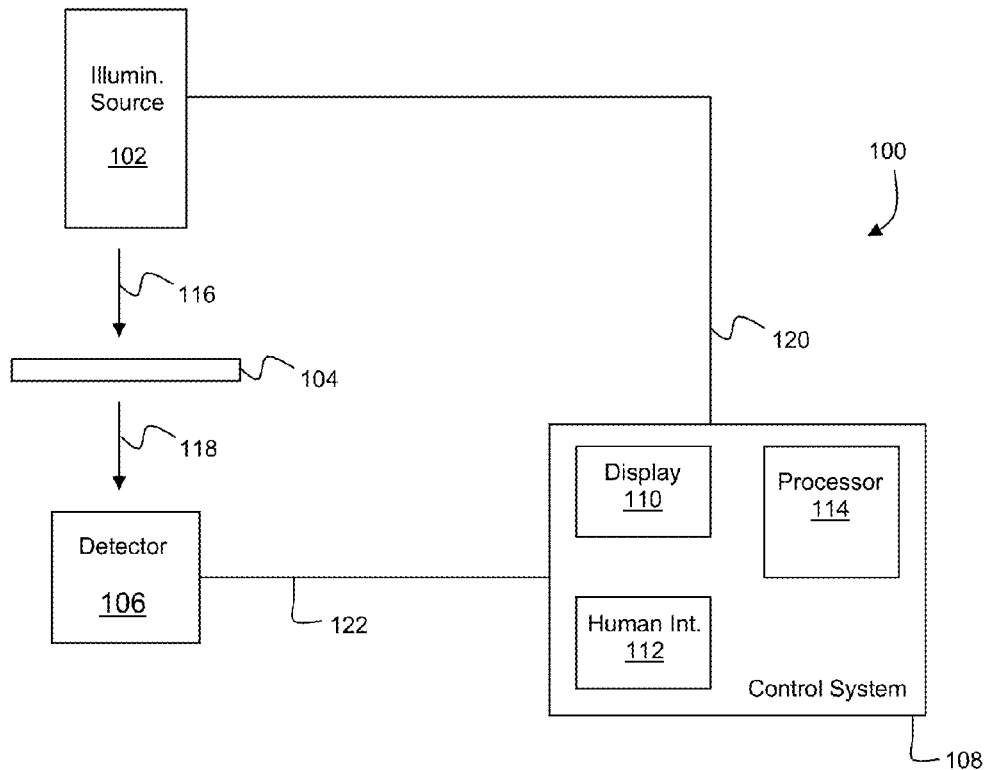
FIG. 1 is a schematic diagram of a system for identifying, quantitating, and measuring features of reticulocytes in a biological sample.

Reticulocytes are immature red blood cells typically characterized by elevated levels of RNA as compared to mature red blood cells. A reticulocyte count performed on a blood sample can provide important information about how quickly a patient's bone marrow is producing red blood cells. Thus, the quantity of reticulocytes in a patient's blood serves as an important diagnostic indicator, and is typically one parameter of a complete blood count. For example, a high reticulocyte count can signify possible internal trauma, blood loss, or certain types of anemia. A low reticulocyte count can signify certain dietary deficiencies (e.g., insufficient iron) or an illness affecting the bone marrow such as cancer. Disclosed herein are methods and systems for automated measurement of cell samples, including the identification, quantitation, and constituent measurement of reticulocytes in the samples. While this disclosure focuses on reticulocyte identification in blood samples from human patients, the disclosure is not limited to such applications. In particular, the methods and systems disclosed herein can be used to measure samples and to identify, in an automated fashion, reticulocytes in quality control compositions intended for use with automated laboratory analyzers or in a variety of different other samples, including samples taken from animals. The methods and systems disclosed herein permit high-throughput, fully-automated analysis of a variety of biological samples extracted from patients, without the need for special stains or other contrast agents specifically designed for reticulocyte identification.

Automated systems for preparing samples for analysis will be described in greater detail below. Once a sample is prepared, it is transported to the automated measurement system. The measurement system acquires one or more two-dimensional images of the cells in the sample, and uses the image(s) to identify reticulocytes among the red blood cells and other formed elements of blood in the image(s) and, in some embodiments, to measure quantities relating to the identified reticulocytes such as reticulocyte volume, area, perimeter, optical density, and/or the amount of one or more constituents (e.g., hemoglobin) in the identified reticulocytes. These quantities are determined from information derived from images of the reticulocytes obtained by directing incident light on the reticulocytes, and then detecting the portion of the incident light that is either transmitted through, or reflected from, the reticulocytes. Each image is a two-dimensional image, where an individual pixel intensity value within the image corresponds to the amount of transmitted or reflected light emerging from a spatial location on the reticulocyte that corresponds to the pixel.

General Considerations

Reticulocytes typically include a network of ribosomal RNA which is present in larger concentrations in reticulocytes than in other types of cells, including mature red blood cells. When certain stains such as azure B and methylene blue are applied to reticulocytes, the stains bind to the RNA. Under microscope examination the stained RNA is readily visible and reticulocytes appear slightly bluer and larger than mature red blood cells. The amount of stained RNA is one criterion that can be used to distinguish reticulocytes from other cell types.

Automated sample preparation systems can apply a variety of different stains to blood samples. While certain conventional techniques for identifying reticulocytes rely on stains specific for binding cellular RNA or other mechanisms specifically intended for reticulocyte identification, the methods and systems disclosed herein advantageously rely on stains that enable automated detection and measurement of all other parameters of a complete blood count including Romanowsky stains. Thus, stains that target both cellular RNA and DNA can be applied to reticulocytes, which can be distinguished from other cell types due to the stained network of ribosomal RNA described above. More generally, cells including red blood cells (e.g., mature erythrocytes, reticulocytes) are typically prepared (as part of a blood sample) by applying one or more stains to a blood sample. The stains bind to the cell cytoplasm, and serve as markers for the cytoplasm in cell images. When the cells are illuminated with incident light, the stain absorbs a portion of the incident light; the amount of absorption at a particular location in the sample depends on the amount of stain present at that location.

In addition to identifying reticulocytes, the methods and systems disclosed herein can be used to determine various properties for the identified reticulocytes. For example, reticulocyte volumes can be determined based on information derived from two-dimensional reticulocyte images by decoupling the estimate of cell thickness from the absorptive effects of locally-varying concentrations of cellular constituents (e.g., hemoglobin) and various applied stains. To implement such decoupling, pixel intensities are scaled according to the maximum pixel intensity for each cell. As further described below, reticulocyte volume calculations can be based on a weighted combination of optical density values for each color of illumination used to acquire reticulocyte images, and reticulocyte area. The processes described herein can be repeated for each member of a set of reticulocytes selected for volume measurement, and the results can be used to calculate a mean reticulocyte volume for the sample. Amounts of reticulocyte constituents, such as hemoglobin content of reticulocytes, also can be determined from calculations based on optical density values for each color of illumination used to acquire reticulocyte images, as will be described further below.

For purposes of the following disclosure, at least two stains are assumed to be applied to the samples: eosin and azure. However, the methods and systems disclosed herein are not limited to application of only two stains or solely to eosin and azure. To the contrary, the methods and systems are capable of performing measurements on samples to which fewer stains (e.g., one stain) or more stains (e.g., a red stain comprising eosin and a blue stain comprising azure and methylene blue, three or more stains, four or more stains, five or more stains) have been applied.

FIG. 1 shows a schematic diagram of a system 100 (which can be part of a larger sample processing and analysis system) for performing automated identification and measurement of reticulocytes in a blood sample. System 100 includes an illumination source 102, a detector 106, and an electronic control system 108. Electronic control system 108 can include a display 110, a human interface unit 112, and an electronic processor 114. Electronic control system 108 is connected to illumination source 102 and to detector 106 via control lines 120 and 122, respectively.

Assuming that a sample has been prepared (as will be discussed further below) for analysis, the prepared sample 104 (e.g., a blood sample deposited on a microscope slide and subsequently fixed, stained, rinsed, and dried) is positioned automatically in proximity to source 102. Source 102 directs incident light 116 toward sample 104. A portion of the incident light passes through sample 104 as transmitted light 118 and is detected by detector 106. Transmitted light 118 forms an image of sample 104 on the active surface of detector 106; the detector captures the image, and then transmits the image information to electronic control system 108. In general, electronic control system 108 directs source 102 to produce incident light 116, and also directs detector 106 to detect the image of sample 104. Control system 108 can instruct source 102 to use different illumination wavelengths when detector 106 acquires images of sample 104 from transmitted light 118.

The process discussed above can be repeated on multiple images of sample 104 if desired. Prior to acquiring a new image, electronic control system 108 can change the wavelength of incident light 116 produced by source 102. As such, the images of sample 104 each correspond to different wavelengths of incident light 116 and therefore, different wavelengths of transmitted light 118. The process repeats until at least enough information has been acquired to perform an accurate identification of red blood cells including reticulocyte candidates and/or determine properties associated with the identified red blood cells and/or reticulocytes.

Typically, the amount of information that yields an accurate identification and/or quantitation of reticulocytes is determined during a calibration process. For example, the calibration process can be used to determine that accurate reticulocyte identification and quantitation can be achieved when the number of sample images obtained is equal to or greater than the number of spectral contributors (e.g., absorbers) factored into the analysis of the sample. As an example, for a prepared sample comprising red blood cells that include hemoglobin as a naturally-present absorber, and eosin and azure as applied stains (for a total of three spectral contributors), system 100 can continue to acquire sample images until it has obtained images at a minimum of three different wavelengths. Additional images—corresponding to further different wavelengths—can also be obtained and used in reticulocyte identification and quantitation.

Illumination source 102 can include one source or a plurality of the same or different sources for directing incident light to a sample. In some embodiments, source 102 can include multiple light emitting elements such as diodes (LEDs), laser diodes, fluorescent lamps, incandescent lamps, and/or flashlamps. For example, source 102 can include four LEDs having output wavelengths in the red, yellow, green, and blue regions of the electromagnetic spectrum, respectively (e.g., 635, 598, 525, and 415 nm), or more generally, about 620 to 750 nm (red), about 575 to 600 nm (yellow), about 525 to 570 nm (green), and about 400 to 475 nm (blue). In certain embodiments, source 102 can include one or more laser sources. Instead of having multiple light emitters, in other embodiments, source 102 can include a single broadband emitter than can be configured to alter its output wavelength (e.g., under the control of electronic control system 108). For example, source 102 can include a broadband source (e.g., an incandescent lamp) coupled to a configurable filter system (e.g., a plurality of mechanically adjustable filters, and/or a liquid-crystal-based electronically-adjustable filter) that produces a variable output spectrum under the control of system 108. In general, source 102 does not output illumination light 116 at a single wavelength, but in a band of wavelengths centered around a central wavelength (e.g., the wavelength of maximum intensity in the band). When the discussion herein refers to the wavelength of illumination light 116, this reference is to the central wavelength of the illumination band.

Detector 106 can include a variety of different types of detectors. In some embodiments, detector 106 includes a charge-coupled device (CCD). In certain embodiments, detector 106 can include photodiodes (e.g., a two-dimensional photodiode array). In some embodiments, detector 106 can include other light-sensitive elements such as CMOS-based sensors and/or photomultipliers. Detector 106 can also include one or more filtering elements, as described above in connection with source 102. In some embodiments, sample images corresponding to different wavelengths are obtained by illuminating sample 104 with illumination light 116 having a relatively broad distribution of wavelengths, and then filtering transmitted light 118 to select only a portion of the transmitted light corresponding to a small band of the wavelengths. Filtering can be performed on either or both the excitation side (e.g., in source 102) and the detection side (e.g., in detector 106) to ensure that images obtained using detector 106 each correspond to a specific distribution of light wavelengths with a particular central wavelength.

General Reticulocyte Identification Methodology

Figure 2:
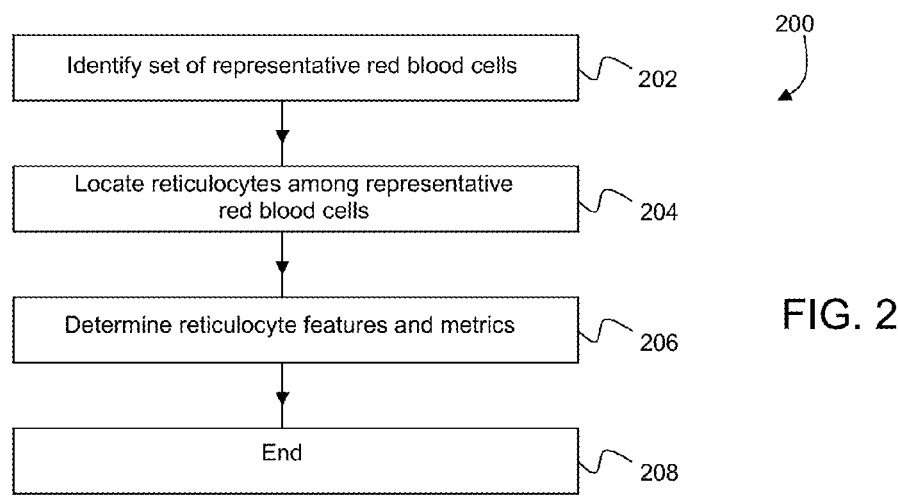
FIG. 2 is a schematic diagram showing a series of steps for identifying reticulocytes in a sample.

The systems and methods disclosed herein acquire images of cells in a sample (e.g., a blood sample deposited on a microscope slide and subsequently prepared for automated microscopic imaging with a fixative and stains) and identify and quantitate reticulocytes from among the cell images. FIG. 2 shows a flowchart 200 that includes various steps for identifying reticulocytes in such images. In a first step 202, a set of representative red blood cells are identified from among all of the white blood cells, red blood cells, platelets, and cellular and non-cellular artifacts in the one or more acquired sample images. In the next step 204, reticulocytes are identified among the set of representative red blood cells. Then, in optional step 206, reticulocyte features and metrics such as reticulocyte volume, the amounts of reticulocyte constituents such as hemoglobin, and reticulocyte geometric parameters can be determined based on the reticulocytes located in step 204. The process terminates at step 208. Each of the steps in flow chart 200 is described in greater detail below.

(i) Reticulocyte Identification

As discussed above, the first step in identifying reticulocytes in a blood sample is the identification of a set of representative red blood cells (of which reticulocytes form a subset) among all of the white blood cells, red blood cells, platelets, and cellular and non-cellular artifacts in the one or more acquired sample images. This step will be discussed in greater detail under the subheading "(ii) Identifying a Set of Representative Red Blood Cells," and can include one or more feature measurement and artifact rejection techniques to identify red blood cells from images of a sample comprising red blood cells, white blood cells, and platelets. After the set of representative red blood cells are identified, reticulocytes are identified among the representative red blood cells by further analysis of each member of the set of red blood cells. Because reticulocytes are immature red blood cells, methods that distinguish red blood cells in a sample from other types of cells (e.g., white blood cells, platelets) can identify both reticulocytes and mature red blood cells together as the set of representative red blood cells. Locating the reticulocytes involves distinguishing between reticulocytes and other more mature red blood cells in the representative set.

In some embodiments, reticulocytes can be located in the representative set based on their absorption spectra, sometimes with the aid of dyes or stains (e.g., using a combination of the fixative, stain, and rinse formulations disclosed in U.S. patent application Ser. No. 13/526,164 filed on Jun. 18, 2012, the entire contents of which are incorporated by reference herein). For example, because reticulocytes contain a network of ribosomal RNA, stains that bind to nucleic acids can be used to identify reticulocytes, since RNA is generally present at elevated concentrations in reticulocytes.

Identifying reticulocytes among the set of representative red blood cells can be determined based on the optical densities of individual cells in the set from images acquired in one or more wavelength regions of the electromagnetic spectrum. For example, in some embodiments, reticulocytes can be located by examining the optical densities of each of the representative red blood cells in sample images acquired in the yellow region of the spectrum. Reticulocytes typically have stronger absorption in the yellow region than mature red blood cells because the nucleic acid stain that is applied to the red blood cells has an absorption peak in the yellow region of the spectrum. For example, Romanowsky stains are often used to mark RNA in red blood cells (including reticulocytes) in a sample.

In certain embodiments, reticulocytes can be located by examining the optical densities of each of the representative red blood cells in sample images acquired in the blue region of the spectrum. Typically, the blue region of the spectrum for purposes of identifying reticulocytes is from 400 nm to 470 nm. Reticulocytes generally have weaker absorption in the blue region than mature red blood cells because the hemoglobin in reticulocytes is not yet fully formed. By comparing the integrated optical density in the blue region for each representative red blood cell to a range of optical density values that are known to correlate with reticulocytes (e.g., from flow cytometry analysis of standardized samples), each representative red blood cell can be classified as either a reticulocyte or a mature red blood cell.

In certain embodiments, the optical densities of red blood cells in multiple spectral regions can be used to identify reticulocytes. For example, reticulocytes can be identified by comparing each representative red blood cell's optical density in images acquired in the blue and yellow regions of the spectrum, respectively (e.g., derived from images of the cell acquired with blue and yellow illumination wavelengths). Reticulocyte identification can be aided by statistical analysis, which is used to reject imaging artifacts.

The first step in determining whether a particular representative red blood cell is a reticulocyte is to determine the color (C) of the cell. For example, a cell's color can be defined as:

$$C = OD_{mean}(b) - OD_{mean}(y) \quad (1)$$

where $OD_{mean}(b)$ is the mean optical density of the entire set of pixels that correspond to the red blood cell using an illumination wavelength in the blue region of the spectrum and $OD_{mean}(y)$ is the mean optical density of the entire set of pixels that correspond to the red blood cell using an illumination wavelength in the yellow region of the spectrum. Determining the set of pixels that correspond to the red blood cell occurs when the red blood cells are individually identified in sample images, and will be discussed later.

The second step in determining whether a particular representative red blood cell is a reticulocyte is to determine the area (A) of the cell based on the set of pixels that corresponds to the cell. Cell areas based on a set of pixels can be determined in various ways, as further discussed later. In some embodiments, the cell area is determined automatically when the set of pixels is identified.

The cell's color C and area A can then be used to determine whether the cell is a reticulocyte by comparing the values of these parameters to cutoff values based on the statistical distributions of the values of these parameters among the entire representative red blood cell population. A particular cell can be identified as a reticulocyte if $$C < C_{cut} \text{ and } A > A_{cut} \quad (2)$$

where $C_{cut}$ is the color cutoff value and $A_{cut}$ is the area cutoff value. Both the color and area cutoff values typically correspond to specific percentile markers within the distributions of color and area among the representative red blood cells. Because reticulocytes generally absorb less strongly in the blue region of the spectrum than mature red blood cells, cells with color C less than the color cutoff value $C_{cut}$ are likely to be reticulocytes. Moreover, because reticulocytes are larger than mature red blood cells, cells with area A larger than the area cutoff value $A_{cut}$ are likely to be reticulocytes. By only identifying cells that satisfy both conditions as reticulocytes, reticulocytes can be located within the larger set of representative red blood cells with high accuracy.

In some embodiments, only one of the conditions in Equation (2) can be used to identify reticulocytes. For example, cells with a color values less than the color cutoff value can be identified as reticulocytes (i.e., $C < C_{cut}$), without consideration of the area of the cells. As another example, cells with areas larger than the area cutoff value can be identified as reticulocytes (i.e., $A > A_{cut}$), without consideration of the color value of the cells.

As discussed above, the color and area cutoff values typically correspond to specific percentiles within the distributions of color and area among the representative red blood cells. By using percentiles (e.g., rather than absolute values), the methods disclosed herein can be used in samples where the staining protocol changes and/or in samples where cell sizes naturally vary from expected cell sizes (e.g., as seen in typical patent-to-patient variation of cell size). For example, the methods can be used to locate reticulocytes among a set of representative red blood cells that are larger, on average, than red blood cells from other patients.

Figure 3A:
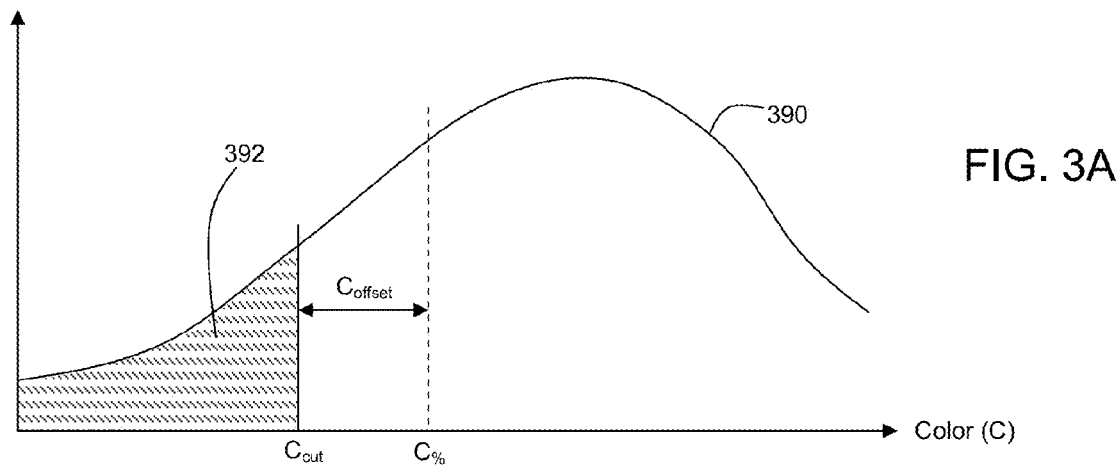
FIG. 3A is a plot showing a color cutoff value for reticulocyte identification among red blood cells in a sample.

In some embodiments, the distribution percentiles are adjusted using offset values to produce the color and area cutoff values. For example, the color and area cutoff values can be expressed as:

$$C_{cut} = C_{\%} + C_{offset} \quad (3)$$

$$A_{cut} = A_{\%} + A_{offset} \quad (4)$$

where $C_{\%}$ and $A_{\%}$ are the color and area percentiles, respectively, and $C_{offset}$ and $A_{offset}$ are the color and area offset values, respectively. FIG. 3A is a histogram showing the color cutoff value $C_{cut}$ that is used to locate reticulocytes among the set of representative red blood cells. In FIG. 3A, the distribution of values 390 of the color parameter C among all of the representative red blood cells is shown. The color percentile marker $C_{\%}$ is also shown within the distribution. Because reticulocytes have color values that are typically smaller than mature red blood cells, the color offset value $C_{offset}$ is a negative value, yielding a color cutoff value $C_{cut}$ that is smaller than the color percentile marker. The shaded region 392 of the distribution corresponds to red blood cells that are identified as reticulocytes based on the color cutoff value.

Figure 3B:
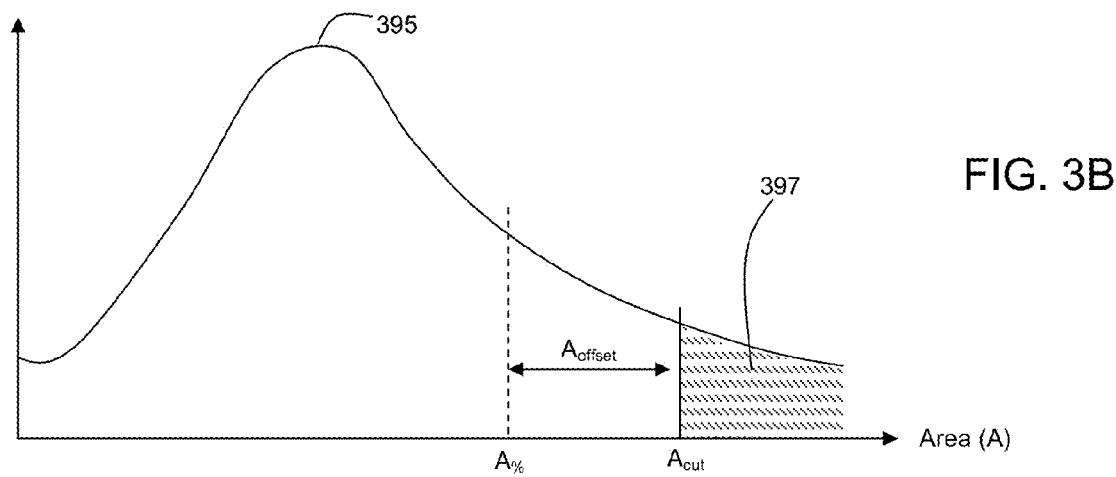
FIG. 3B is a plot showing an area cutoff value for reticulocyte identification among red blood cells in a sample.

FIG. 3B is a histogram showing the area cutoff value $A_{cut}$ that is used to locate reticulocytes among the set of representative red blood cells. In FIG. 3B, the distribution of areas 395 among all of the representative red blood cells is shown. The area percentile marker $A_{\%}$ is also shown within the distribution. Because reticulocytes have areas that are typically larger than those of mature red blood cells, the area offset value $A_{offset}$ is a positive value, yielding an area cutoff value $A_{cut}$ that is larger than the area percentile marker. The shaded region 397 of the distribution corresponds to red blood cells that are identified as reticulocytes based on the area cutoff value.

Specific values for the color and area percentiles and offsets can be determined by analyzing a training data set containing samples with known mature red blood cell and reticulocyte populations. The training data set typically includes hundreds or thousands of samples; the mature red blood cell and reticulocyte populations can be measured in these samples manually by a laboratory technician or using a properly calibrated flow cytometry system. Then, the training set is analyzed using the methods and systems disclosed herein, and the percentiles and offset values are selected to best match the experimental analysis results to the known measurements from the training data set.

As an example, in some embodiments, the color percentile marker is the 70th percentile, and the color offset value is −0.09. More generally, the color percentile marker can be the 80th percentile or less (e.g., 60th percentile or less, 50th percentile or less, 40th percentile or less). Typically, but not always, if the color percentile marker is less than the 70th percentile, the color offset value is larger than −0.09.

As another example, in some embodiments, the area percentile marker is the 20th percentile, and the area offset value is 12.4. More generally, the area percentile marker can be the 10th percentile or more (e.g., 30th percentile or more, 40th percentile or more, 50th percentile or more, 60th percentile or more). Typically, but not always, if the area percentile marker is more than the 20th percentile, the area offset value is smaller than 12.4.

In some embodiments, one or more artifact rejection steps are optionally performed to further refine the identification of reticulocytes from among the set of representative red blood cells. These artifact rejection steps can be performed before the comparisons described above to color and area cutoff values, after the comparisons, or both before and after. As an example, artifact rejection steps based on statistical analyses of optical densities of the pixels corresponding to a particular representative cell at different wavelengths can be used to reject the cell as an artifact rather than a cell. Optical densities at a variety of wavelengths (e.g., illumination wavelengths) can be used for artifact rejection. Blue, yellow, and green wavelengths, as an example, have been found to be useful for this purpose.

In general, a cell having an associated set of pixels for which the standard deviation of the optical densities of the pixels is large can be classified as an artifact rather than a cell because high standard deviations can indicate unusual cell morphology, overlapping cells, and/or poor cell preservation. Such cells are generally unsuitable for further analysis. As an example, a cell having an associated set of pixels can be rejected as artifact if:

$$\sigma_{OD}(y) > \sigma_y \text{ or } \sigma_{OD}(g) > \sigma_g \text{ or } \sigma_{OD}(b) > \sigma_b \qquad (5)$$

where $\sigma_{OD}(y)$, $\sigma_{OD}(g)$, and $\sigma_{OD}(b)$ are the standard deviations of the optical densities of the set of pixels corresponding to images acquired with yellow, green, and blue illumination wavelengths, respectively, and $\sigma_y$, $\sigma_g$, and $\sigma_b$ are standard deviation cutoff values. In general, suitable standard deviation cutoff values can be determined from the analysis of training data as described above and/or from historical data (e.g., data from prior analyses of cell images). In some embodiments, for example, suitable standard deviation cutoff values are $\sigma_y=0.1$, $\sigma_g=0.099$, and $\sigma_b=0.058$. These values can be changed according to the nature of the sample, the staining protocol, and the imaging conditions. As an example, in certain embodiments, suitable standard deviation cutoff values are $\sigma_y=0.079$, $\sigma_g=0.085$, and $\sigma_b=0.060$.

The reticulocyte identification embodiments described above can also be used to identify reticulocytes in quality control compositions intended for use with automated sample measurement systems such as the systems disclosed herein. Quality control compositions typically include various types of preserved mammalian blood cells, and are designed to mimic whole blood samples when processed on an automated system. In turn, the analysis results of these samples can be used to assess the performance of the automated system, for example, the system accuracy and reproducibility for identifying reticulocytes. In certain quality control compositions, the preservation process significantly reduces the size of the reticulocytes in the control sample compared to reticulocytes in a patient sample of blood; in certain instances, the reticulocytes in such compositions are smaller than the mature red blood cell components. Thus, reticulocyte identification embodiments relying on the color analysis described above, without using the area analysis, can be used to accurately detect reticulocytes within certain quality control compositions.

(ii) Identifying a Set of Representative Red Blood Cells

Returning to FIG. 2, the first step 202 in flow chart 200 involves identifying a set of representative red blood cells from among the cells in the image(s) of the sample that are acquired using the systems and methods disclosed herein. Reticulocyte identification in step 204 occurs after the set of representative red blood cells has been identified from images of the sample; thus, the set of representative red blood cells typically includes mature erythrocytes and reticulocytes. Then, in optional step 206, one or more reticulocyte features and metrics are determined such as, for example, reticulocyte hemoglobin measurements. For purposes of this disclosure, the determination of reticulocyte features and metrics is shown as a separate step 206. However, in some embodiments, certain reticulocyte features and metrics such as area, perimeter, and shape are measured as part of step 202 (e.g., the identification of a set of representative red blood cells). This step 202 of identifying a set of representative red blood cells will now be described in greater detail.

Utilizing images acquired via detector 106, intensity values for each pixel in a sample image can be correlated to an optical density value used in the selection of a representative set of cells and subsequent artifact rejection, feature measurement, and reticulocyte identification. The transmitted light intensity $T(x,y)$ at a given image pixel $(x,y)$ is related to the absorption coefficient $\alpha$ and the path length $\epsilon(x,y)$ of the incident light through the portion of the sample corresponding to that pixel:

$$T(x,y)=10^{-\alpha \cdot \epsilon(x,y)} \qquad (6)$$

For each pixel in an image, the ratio of the pixel intensity to the maximum possible pixel intensity (e.g., pixel intensity/255 at 8-bit resolution) represents the fraction of light transmitted at the spatial location of the pixel. The fraction of transmitted light can be expressed in optical density (OD) units by taking the logarithm of Equation (6):

$$OD(x,y) = -\log(T) = \alpha \cdot \epsilon(x,y) \qquad (7)$$

This process can be repeated for each pixel in the sample image. In this way, the optical density at each pixel in each image corresponds to the total amount (e.g., the product of the absorption coefficient and the thickness) of absorbing material in the sample at the location corresponding to the pixel.

Figure 4:
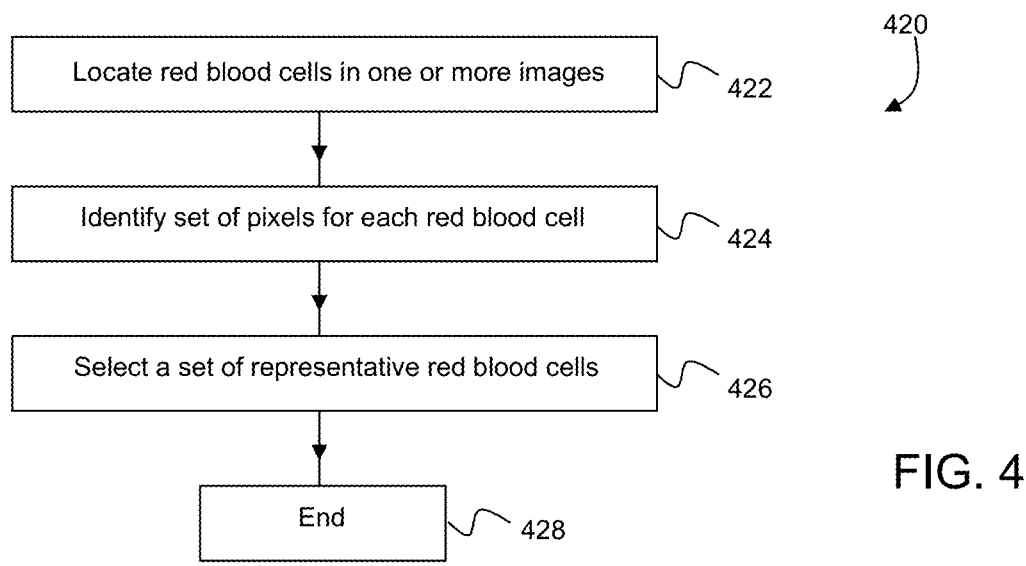
FIG. 4 is a schematic diagram showing a series of steps for selecting a representative set of red blood cells from one or more images of a sample.

FIG. 4 shows a flowchart 420 that includes a series of steps for selecting a set of representative red blood cells from images of a prepared sample of blood. After acquiring images of the sample, electronic control system 108 and, in particular electronic processor 114, processes the image information to differentiate cells for inclusion in the set of representative red blood cells from the other cell types (e.g., white blood cells and platelets), cell clusters, and artifacts present in the sample.

First, in step 422 of FIG. 4, system 100 locates red blood cells (e.g., mature red blood cells and reticulocytes) in one or more sample images for further processing. Red blood cells typically absorb blue light (e.g., 415 nm) due to the presence of hemoglobin in the cells. White blood cells, however, do not contain hemoglobin and therefore do not absorb blue light in the same manner as red blood cells. An image of the sample acquired under blue light can be used to identify red blood cells; white blood cells in such images appear faintly and distorted because these cells minimally absorb blue light, thereby reducing contributions to the image and typically making them unidentifiable.

In some embodiments, a thresholding step can be used to ensure that system 100 identifies only red blood cells for further analysis. For example, system 100 can utilize only image pixels below an intensity (or gray) value of 160 (for images captured at 8-bit resolution). Other intensity value thresholds ranging from 100 to 180 can be used to identify red blood cells from the image, while excluding white blood cells from further analysis.

Next, in step 424, system 100 identifies a set of pixels for each red blood cell in the sample image. A variety of different methods can be used to identify sets of pixels associated with the cells. For example, in some embodiments, system 100 performs the identification step using a connected components labeling process. This process correlates individual pixels from the sample image to an object in the image. For example, any two pixels in the image not separated by a pixel assigned to the background are assigned to the same cell.

In addition, system 100 can exclude pixels positioned within a border region of a cell from certain measurements relating to, for example, cell volume or constituent analysis. In particular, red blood cells often have thick, dark borders due to the manner in which these cells refract illumination light. Optical densities for these pixels are typically unreliable due to this refraction. After completing the connected components labeling process, system 100 can apply a pixel erosion mask to the identified cells to remove the outermost n layers of pixels (e.g., the pixel(s) that correspond to the boundary region where refraction is greatest). In general, the pixel erosion mask can be selected to remove any number n of pixel layers (e.g., one pixel layer or more, two pixel layers or more, three pixel layers or more, four pixel layers or more, five pixel layers or more, six pixel layers or more, eight pixel layers or more, ten pixel layers or more) depending on the magnification of the image. For example, it has been determined experimentally that a pixel erosion mask comprising the outermost 0.5 µm for the red cell perimeter is generally suitable for significantly reducing erroneous contributions to the measurement of cell volume and hemoglobin content for red blood cells where each pixel corresponds to a portion of the cell that is 0.148 µm×0.148 µm. Utilizing the sets of pixels corrected by erosion masks, various cell features can be measured, such as a mean and maximum optical density for each cell, which contribute to the cell volume and constituent analysis.

In step 426, system 100 continues the process of identifying a set of representative red blood cells from the sample image(s) by confirming that the set contains only complete and normally shaped and sized red blood cells. In general, step 426 functions to discard partial cells, overlapping cells, cell clusters, platelets, and non-cellular artifacts from inclusion in the set of representative red blood cells. For example, cells that are either cut off by, or touching, the edge of the image frame can be excluded from further analysis, thereby preventing inaccurate measurements. In addition, misshapen cells—which can exhibit variations in the determined cell volume that are related to their non-standard shapes—can be excluded from the analysis. Further, measurement results obtained from overlapping cells, which can be unreliable when used for calculating cell volumes or constituent content, can be precluded from the set of representative cells. For these reasons, the shapes of each of the identified cells are checked in step 426, and misshapen and/or overlapping cells are excluded from further analysis.

Figure 5:
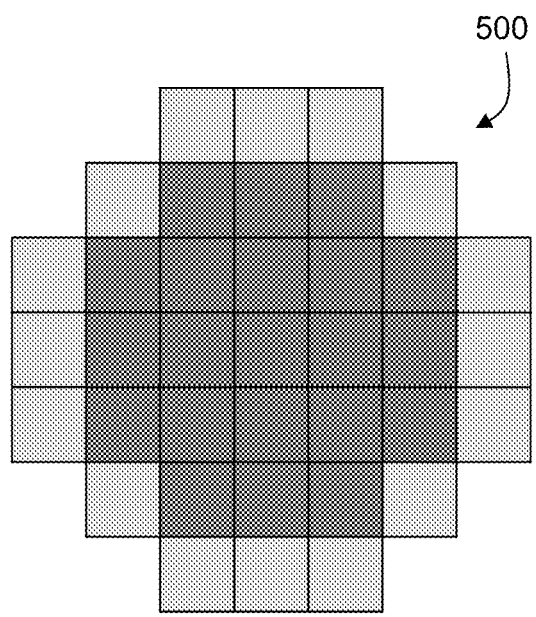
FIG. 5 is a schematic image of a cell showing the cell boundary.

A variety of different methods can be used to check the shape of the identified cells. For example, in some embodiments, the shape of each cell can be checked by comparing the perimeter and the area of the cell. FIG. 5 shows a schematic diagram of such a comparison. In FIG. 5, a cell 500 has been identified as a set of pixels in a sample image. The pixels corresponding to the boundary of cell 500 are shaded lighter in FIG. 5 than the interior pixels for purposes of demonstration—they do not necessarily appear this way in the actual image. The area of cell 500 can be determined by counting the number of pixels in the set.

The cell perimeter is determined from the boundary pixels using the set of pixels corresponding to cell 500. This can be accomplished by connecting a line through the center of each perimeter pixel to create a polygon in the image and measuring the perimeter of the polygon. The ratio of this cell perimeter value squared to the cell area value (i.e., the area of the polygon) is determined to check the shape of the cell. The value of this ratio is $4\pi$ for an ideal, perfectly circular cell. The value of the ratio increases as the cell shape departs from a circular outline. Using this criterion, cells with a ratio of the perimeter squared to the area, which exceeds the minimum value of $4\pi$ by a threshold amount or more, are excluded from further analysis. Typically, the threshold amount is a percentage of the minimum value of $4\pi$ (e.g., 5% or more, 10% or more, 15% or more, 20% or more, 25% or more).

In addition to excluding misshapen individual cells from further analysis, the procedure discussed above can also exclude overlapping cells. In sample images, overlapping cells typically appear as large, misshapen individual cells (with variations in transmitted light intensity due to the increased thickness of material through which the incident light propagates). Overlapping cells are generally identified as large single cells with irregular boundaries when analysis algorithms are applied to such images. As such, when the comparison of the cell perimeter and area is performed, the ratio falls well beyond the threshold for allowable variance from the ideal value, and the overlapping cells are excluded.

Figure 6:
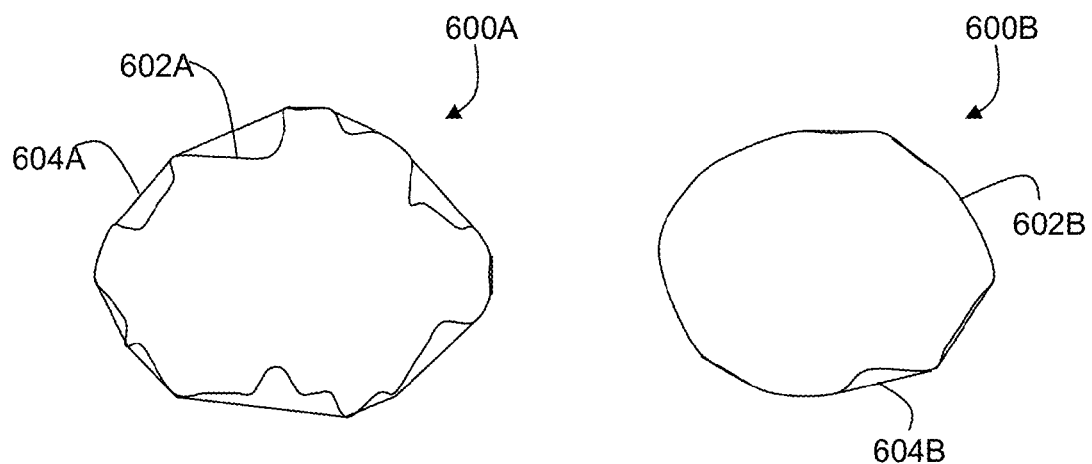
FIG. 6 is a schematic diagram showing two cells and convex hulls determined for each of the cells.

Another method for checking the shape of identified cells utilizes the convex hull of the polygonal representation of the cell outline described above and compares the area enclosed by the convex hull to the cell area determined from the image pixels. A high ratio of convex hull area to cell area can be used to identify irregularly shaped cells and exclude such cells from further analysis. FIG. 6 is a schematic diagram that includes two cells 600A and 600B. The perimeters of cells 600A and 600B are marked as 602A and 602B, respectively, in FIG. 6. A convex hull 604A is drawn around cell 600A, and a convex hull 604B is drawn around cell 600B. As shown in FIG. 6, the discrepancy between the convex hull area and the cell area is greater for cell 600A than for cell 600B. Given the high degree of irregularity for cell 600A, cell 600A can be excluded from the set of representative red blood cells.

In some embodiments, cell area measurements can be used in step 426 to exclude artifacts and overlapping cells from the set of representative blood cells. For example, only cells with an area ranging from 35 square microns to 65 square microns can be considered for red blood cell measurements including reticulocyte identification. Imaged objects with an area less than 35 square microns are typically not red blood cells, but artifacts, such as a speck of dust in the sample. Similarly, imaged objects with an area greater than 65 square microns are typically not red blood cells; such object might correspond to a blob of stain or to several overlapping cells. While the foregoing example describes a 35 to 65 square micron area range, other ranges can be used to select red blood cells for measurement (e.g., 20 square microns to 80 square microns), and the range can be scaled based on the average cell size in the sample, thereby accounting for patient-to-patient variability. It has been determined experimentally that while the 35-to-65 square micron range can exclude some red blood cells, such range is more effective at removing artifacts from the sample image as compared to the 20-to-80 square micron range.

Optical density values can be used to select the set of representative red blood cells in the sample. For example, if the mean optical density value of an object imaged under blue light is too low, the object may be a white blood cell nucleus instead of a red blood cell. A mean optical density threshold can be used (e.g., mean optical density less than or equal to 0.33) for images acquired using blue light to exclude white blood cells from the set of representative red blood cells for the sample (e.g., a cell with a mean optical density less than or equal to 0.33 is likely to be a white blood cell). For images acquired under blue or yellow illumination, a mean optical density value for an object exceeding a certain threshold (e.g., mean optical density greater than or equal to 0.66) can be used to identify stacked, overlapping, and/or clustered red blood cells, which can be excluded from further analysis (e.g., a red blood cell with a mean optical density greater than or equal to 0.66 is likely to be overlapping another red blood cell).

The process shown in FIG. 4 terminates at step 428 with the final determination of a set of representative cells for further analysis. As previously described, the reticulocyte identification process can then proceed using measured features of the cells within the representative set.

(iii) Determining Reticulocyte Metrics and Features

Returning to FIG. 2, after the set of representative red blood cells has been identified in step 202 and the reticulocytes have been located (and optionally counted among the red blood cells in step 204, one or more reticulocyte metrics and features can optionally be determined in step 206. As discussed above, some reticulocyte features, including reticulocyte area, shape, perimeter, size, and optical density, can be determined during step 202 while identifying the set of representative red blood cells. These features can also be determined in step 206. In addition, other features and metrics associated with the reticulocytes can be determined in step 206. For example, the systems and methods disclosed herein can use combinations of reticulocyte image features to calculate reticulocyte metrics such as volume and constituent values such as hemoglobin content. The combinations typically include (but are not limited to) linear combinations of such reticulocyte features that the inventors have discovered yield accurate, reproducible results for a wide variety of samples.

Figure 7:
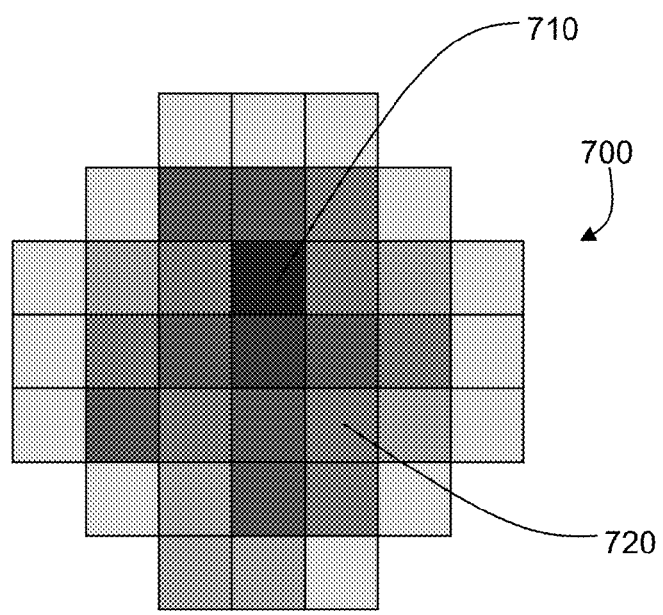
FIG. 7 is a schematic image of a cell showing variations in optical density among cell pixels.

Once the reticulocytes have been located among the set of representative red blood cells as described above, some or all of the features disclosed herein can be calculated for each reticulocyte based on one or more images of the cell obtained by system 100. A first set of features that can be calculated for the reticulocytes is the color-specific integrated optical density, IOD(c), which can be determined as follows:

$$\text{IOD}(c) = A \cdot \text{OD}_{mean}(c) \tag{8}$$

where A is the area of the reticulocyte, and $\text{OD}_{mean}(c)$ is the mean optical density of pixels in the image of the reticulocyte when the reticulocyte is illuminated with light of color c. If images of a reticulocyte are obtained at different illumination wavelengths, a value of IOD(c) can be calculated for the reticulocyte at each illumination wavelength. FIG. 7 shows a schematic image, obtained with illumination light of color c, of a representative reticulocyte 700 identified through the process described in connection with flowchart 420. The image of reticulocyte 700 includes a plurality of pixels. The mean optical density of pixels in reticulocyte 700, $\text{OD}_{mean}(c)$, corresponds to the sum of the pixel intensities in FIG. 7 divided by the number of pixels in the image.

A second set of features that can be calculated for each reticulocyte is the color-specific volume of the reticulocyte, Vol(c). The volume of reticulocyte 700 in FIG. 7 is calculated by summing optical density values for each of the pixels that correspond to reticulocyte 700. First, the "height" of reticulocyte 700 at each pixel can be estimated as:

$$\text{height} = \frac{OD_{pixel}}{OD_{max}} \tag{9}$$

where $OD_{pixel}$ is the optical density associated with the given pixel, and $OD_{max}$ is the maximum optical density among all optical densities associated with the reticulocyte pixels. Thus, for example, pixel 720 in the image of reticulocyte 700 has an optical density that is smaller than the maximum optical density associated with pixel 710. The contribution of pixel 720 to the volume of reticulocyte 700 is the ratio $OD_{720}/OD_{max}$, where $OD_{720}$ is the optical density of pixel 720 and $OD_{max}$ is the optical density of pixel 710. Then, the color-specific reticulocyte volume, V, is calculated by summing the ratio of pixel optical density to maximum optical density for all pixels in reticulocyte 700:

$$V = \sum_{pixels} \frac{OD_{pixel}}{OD_{max}} = \frac{\sum_{pixels} OD_{pixel}}{OD_{max}} = \frac{N_{pixels} \cdot OD_{mean}}{OD_{max}} \tag{10}$$

where the sum of the optical densities associated with each of the pixels in reticulocyte 700 is replaced in Equation (10) by the product of the number of pixels in reticulocyte 700, $N_{pixels}$, and the mean pixel optical density for the pixels in reticulocyte 700, $OD_{mean}$.

Typically, the optical density values for pixels near the edge of a reticulocyte are not a valid contributor to the color-specific volume measurement because light refracted at the edge of the cell creates an artificially dark border around the reticulocyte. To avoid this effect from such border pixels, the system can erode the mask at the reticulocyte periphery by one or more pixels as previously described, measure the mean optical density and the maximum optical density of the masked region of the reticulocyte, and, thereafter, extrapolate to the edge of the reticulocyte by multiplying by the area of the full, non-eroded mask.

Further, when multiple images corresponding to different illumination wavelengths are used to obtain images of a single reticulocyte, a reticulocyte volume calculation determination can be made at each color of illumination light. Accordingly, the color-specific reticulocyte volume can be determined as:

$$Vol(c) = \frac{A \cdot OD_{mean}(c)}{OD_{max}(c)} \qquad (11)$$

where A is the area of the entire reticulocyte including the cell periphery, $OD_{mean}(c)$ is the color-specific mean optical density for pixels within the masked region of the reticulocyte, and $OD_{max}(c)$ is the color-specific maximum optical density for the eroded mask of the reticulocyte (e.g., pixel 710 in FIG. 7). The calculated color-specific reticulocyte volume Vol(c) can be scaled to express the reticulocyte volume in appropriate units (e.g., femtoliters).

In some embodiments, it is useful to add one or more correction factors to Equation (11) to adjust for the fact that some of the darkness of a reticulocyte image may not truly be due to the RNA or hemoglobin content of the reticulocyte. In addition, a scaling factor can be applied to convert the volume measurement to a unit of measurement such as femtoliters (fL). To account for these correction and scaling factors, Equation (11) can be rewritten as:

$$Vol(c) = \frac{S \cdot [A \cdot OD_{mean}(c)]}{OD_{max}(c) + J} + B \qquad (12)$$

where S corresponds to a scaling factor or slope, J corresponds to a correction factor to account for bias in the determination of maximum optical density, and B corresponds to an intercept value that corresponds to a global offset value.

The correction factor, scaling factor, and intercept value can be determined experimentally using a data set of known volume values for multiple blood samples processed on, for example, a calibrated flow cytometer. A slightly different set of correction factors will, in general, provide the best result for each different sample, although correction factors can be determined based on the results across an entire data set. For example, for a data set containing known reticulocyte volume values for 1,000 blood samples, a correction factor that works best on average across the entire data set can be determined by selecting the correction factor that minimizes the sum of squared differences between measured and expected volume values across the entire data set. A scaling factor can be determined across the entire data set by selecting the scaling factor that best converts raw volume values to a desirable measurement unit such as femtoliters. The intercept value B can be selected for the data set to ensure that Equation (12) passes through the origin when the data are presented on a two-dimensional plot. The correction factor, scaling factor, and intercept value can be stored in a memory unit associated with electronic control system 108, and retrieved from memory when determining color-specific reticulocyte volumes as shown in Equation (12) for analysis of new samples.

Using Equation (8) and Equation (11) or (12), two features (e.g., integrated optical density IOD(c) and volume Vol(c)) can be determined for each color of illumination light used to obtain sample images. For example, if four different colors of illumination light are used, a total of eight different features can be determined for each reticulocyte identified from the representative set. In addition, as explained above, the area A of each individual reticulocyte can be determined from an image of the reticulocyte. The color-specific integrated optical densities and reticulocyte volumes, and the reticulocyte area, can then be used to calculate various metrics for each reticulocyte.

Reticulocyte metrics such as reticulocyte volume and constituent amounts can be calculated based on weighted combinations of some or all of the features calculated for the reticulocytes disclosed above. In general, a metric M can be determined according to:

$$M = \sum_n [\omega_{n,i} \cdot IOD(n) + \omega_{n,v} \cdot Vol(n)] + \omega_a \cdot A + K \qquad (13)$$

where n corresponds to each of the colors of illumination light used to obtain images of the reticulocyte, the $\omega_{n,i}$ values are color-specific weight coefficients for each of the color-specific integrated optical densities IOD(n), the $\omega_{n,v}$ values are color-specific weight coefficients for each of the color-specific volumes Vol(n), $\omega_a$ is a weight coefficient for the reticulocyte area A, and K is an offset value. For example, when four different illumination wavelengths are used to obtain images of reticulocytes (e.g., red=r, yellow=y, green=g, and blue=b), then the volume of a reticulocyte, V, can be determined as:

$$V = \omega_{r,i} \cdot IOD(r) + \omega_{y,i} \cdot IOD(y) + \qquad (14)$$
$$\omega_{g,i} \cdot IOD(g) + \omega_{b,i} \cdot IOD(b) + \omega_{r,v} \cdot Vol(r) +$$
$$\omega_{y,v} \cdot Vol(y) + \omega_{g,v} \cdot Vol(g) + \omega_{b,v} \cdot Vol(b) + \omega_a \cdot A + K$$

Amounts of reticulocyte constituents can be determined in similar fashion. For example, a concentration of hemoglobin in a reticulocyte, H, can be calculated according to:

$$H = \omega_{r,i} \cdot IOD(r) + \omega_{y,i} \cdot IOD(y) + \omega_{g,i} \cdot IOD(g) + \qquad (15)$$
$$\omega_{b,i} \cdot IOD(b) + \omega_{r,v} \cdot Vol(r) + \omega_{y,v} \cdot Vol(y) +$$
$$\omega_{g,v} \cdot Vol(g) + \omega_{b,v} \cdot Vol(b) + \omega_a \cdot A + K$$

The difference between Equations (14) and (15) above is in the values of the weight coefficients and the offset K. Using Equations (14) and (15), reticulocyte volumes and constituent amounts (e.g., the amount of hemoglobin) can be determined for multiple reticulocytes in the sample. The results can be averaged to determine mean reticulocyte volume and mean concentrations of constituents (e.g., mean reticulocyte hemoglobin) for the sample.

The weight coefficients associated with the color-specific features in Equation (13) can be determined based on available training data, for example, by determining linear regression coefficients that map the experimentally determined sample features onto training data comprising known volume and/or constituent concentration values for such samples. Using a linear regression approach to determine color-specific weights can improve the accuracy of sample mean reticulocyte volume and mean reticulocyte constituent concentration measurements by correcting for uncontrollable factors that impact measurements such as cell-to-cell variability in membrane thickness and stain absorption. After color-specific weight values have been determined from training data, the weight values can be stored and later retrieved from a storage unit (e.g., an electronic memory unit) prior to analysis of each sample.

In general, a wide variety of different samples can be used to determine appropriate weight coefficients. To obtain highly reproducible results, it can be advantageous to use training data that span the entire range of values of quantities that are calculated. Further, if samples to be analyzed include unusual morphological features such as cell clumps, it can be advantageous to use training data that include representative samples of such features.

As an example, after determining a set of weight coefficients from a set of training data for the determination of reticulocyte volume, Equation (14) can be re-written as follows:

$$V = (-4.04) \cdot IOD(r) + 8.49 \cdot IOD(y) + (-3.69) \cdot IOD(g) + \\ 4.40 \cdot IOD(b) + 4.68 \cdot Vol(r) + (-8.20) \cdot Vol(y) + \\ 3.57 \cdot Vol(g) + 0.0159 \cdot Vol(b) + (-0.125)A + 4.84 \quad (16)$$

Similarly, after determining suitable weight coefficients from a set of training data for the determination of reticulocyte hemoglobin, Equation (15) can be re-written as:

$$H = (-1.05) \cdot IOD(r) + (-2.44) \cdot IOD(y) + 1.12 \cdot IOD(g) + \\ 2.15 \cdot IOD(b) + 1.95 \cdot Vol(r) + (-0.112) \cdot Vol(y) + \\ (-1.27) \cdot Vol(g) + 0.457 \cdot Vol(b) + (-0.221) \cdot A + -5.73 \quad (17)$$

Additional details regarding cell volume and cell constituent content measurement techniques are disclosed in co-pending U.S. patent application Ser. Nos. 13/446,967 and 13/447,045 filed on Apr. 13, 2012, the contents of which are incorporated herein by reference in their entirety.

As previously described, the systems and methods disclosed herein can be used to analyze both whole blood samples (e.g., samples taken from patients) and quality control compositions. The weight coefficients shown in Equations (14)-(17) can be used to analyze both whole blood samples and quality control compositions. In other embodiments, weight coefficients specific for quality control compositions can be used; as previously described in connection with patient blood samples, such coefficients can be determined using training data comprising known, measured values of reticulocytes in quality control compositions.

In some embodiments, a device can be used to analyze control compositions to assess the accuracy of the results produced by the device. For example, results from analysis of control compositions by the device (e.g., the determination of reticulocyte quantities and one or more other metrics such as reticulocyte hemoglobin, reticulocyte volume, mean reticulocyte hemoglobin, and mean reticulocyte volume) can be compared to reference values of these quantities for the control compositions to assess the device's accuracy. If a difference between the determined and reference values for one or more of these quantities exceeds a threshold value, the device can be re-calibrated. Re-calibration can include, for example, re-determining values of some or all of the weight coefficients in Equations (14)-(17) from reference blood samples, as described herein.

Additional Embodiments

In Equations (14)-(17), four colors of illumination light (red, yellow, green, and blue) are used to illuminate the sample, and integrated optical densities and reticulocyte volumes are calculated from images that correspond to each of these colors. The illumination wavelengths used to calculate the color-specific integrated optical density values and volumes can be, e.g., 635 nm, 598 nm, 525 nm, and 415 nm, although other values within the red, yellow, green, and blue regions of the electromagnetic spectrum can be used in other embodiments. More generally, different numbers of illumination wavelengths can be used, and images corresponding to each of the illumination wavelengths can be obtained and used to calculate color-specific values of integrated optical density and/or reticulocyte volume. For example, in some embodiments, three different wavelengths of light are used to illuminate a sample. In certain embodiments, more than four wavelengths (e.g., five wavelengths, six wavelengths, seven wavelengths, eight wavelengths, ten) of illumination light can be used, and color-specific integrated optical densities, cell volumes, and weight coefficients can be determined at some or all of the illumination wavelengths. In general, the wavelengths of illumination light can be selected such that each image at each of the different wavelengths include different information about the sample. For example, if the sample includes three spectral contributors, three wavelengths of illumination light can be selected for use such that each of the three wavelengths is most strongly absorbed by a different one of the spectral contributors.

As discussed above, color-specific weight coefficients in Equation (13) can be determined by mapping linear regression coefficients for experimentally determined features for a large number (e.g., 1,000) of blood samples onto a training data set comprising known values of reticulocyte volume and/or concentrations of various reticulocyte constituents for such samples, obtained for example from a calibrated flow cytometry system. With changes to sample preparation parameters (e.g., modifications to stain compositions affecting the appearance of stained reticulocytes or other factors impacting how reticulocytes absorb stain such as the extent of sample drying before fixing and staining), the process of determining color-specific weights and an intercept value for Equation (13) can be repeated to ensure determination of accurate volume and reticulocyte constituent measurement values for a given set of sample preparation parameters. However, once sample preparation parameters have been optimized for a particular sample preparation system, the experimentally derived weight coefficients and other parameter values in Equation (13) will generate accurate and reproducible measurements of reticulocyte volume and/or reticulocyte constituent amounts.

In Equation (13), metric M is calculated as a weighted linear combination of the color-specific integrated optical densities, the color-specific volumes, and the reticulocyte area. Not all of these features are used to determine values of metrics in all embodiments, however. For example, in some embodiments, a metric M can be calculated as a weighted combination of only the color-specific integrated optical densities or the color-specific volumes. In certain embodiments, a metric M can be calculated as a weighted combination of the reticulocyte area and either the color-specific integrated optical densities or the color-specific volumes. In some embodiments, a metric M can be calculated as a weighted linear combination of the color-specific integrated optical densities and the color-specific volumes. In general, a suitable combination of features used to calculate a particular metric M can be determined using reference samples for which values of the metric M are known.

When determining the amount of a particular constituent in reticulocytes, if only a single spectral contributor is present in the sample (e.g., an absorptive contributor such as hemoglobin), than the total amount of that contributor present in a particular reticulocyte can be determined by summing intensity contributions from each of the pixels in the image that correspond to the selected reticulocyte. As the intensity contributions correspond only to absorption by hemoglobin, only one sample image would be needed to determine the total amount of hemoglobin present in the reticulocyte.

In practice, however, samples are typically prepared with one or more stains to assist a technologist or an automated imaging system to identify, count and classify various cell types. With multiple spectral contributors in the sample, the absorption at each illumination wavelength is a combination of absorption due to each contributor in the sample; the total contribution at any wavelength for a particular reticulocyte still corresponds to the sum of contributions at that wavelength from each of the pixels representing the reticulocyte. Thus, with spectral contributors hemoglobin (H), eosin (E), and azure (A) present in the sample, and assuming that three images of the sample correspond to illumination light having central wavelengths in the yellow (y), green (g), and blue (b) regions of the electromagnetic spectrum, the optical densities OD at each of these three wavelengths for a particular reticulocyte (or for all pixels in the image that correspond to one or more reticulocytes) can be assumed to be a linear combination of the absorption due to each of the spectral constituents at each wavelength:

$$OD(y) = H \cdot \alpha_{y,H} + E \cdot \alpha_{y,E} + A \cdot \alpha_{y,A}$$

$$OD(g) = H \cdot \alpha_{g,H} + E \cdot \alpha_{g,E} + A \cdot \alpha_{g,A}$$

$$OD(b) = H \cdot \alpha_{b,H} + E \cdot \alpha_{b,E} + A \cdot \alpha_{b,A} \quad (18)$$

where $\alpha_{i,j}$ is the absorption coefficient for spectral contributor j (e.g., hemoglobin H, eosin E, or azure A) at wavelength i (e.g., yellow y, green g, or blue b).

Each of the central wavelengths of light can be determined by passing a known spectrum of light through the sample to the detector and measuring the absorbance of the sample. For example, the detector can acquire three images of the sample using an illumination source with narrow illumination spectra in the yellow, green, and blue regions, respectively. Where each spectral contributor has an absorption spectrum containing a local maximum, illumination sources can be selected such that the emission spectra correspond to or best approximate the spectral contributor local maxima. For example, the blue illumination can be selected as the wavelength that corresponds to the peak absorbance of hemoglobin in the sample (e.g., 415 nm). The yellow illumination can be correlated to the wavelength that corresponds to the peak absorbance of azure stain in the sample (e.g., 598 nm). Similarly, the green illumination wavelength can be selected at the wavelength that corresponds to the peak absorbance of eosin stain in the sample (e.g., 525 nm). Additional illumination wavelengths can be selected to correlate with peak absorbance values for additional spectral contributors in the sample.

The optical density quantities OD(y), OD(g), and OD(b) can be determined from the image information, and the absorption coefficients $\alpha_{i,j}$ can be obtained from literature sources or determined experimentally. Thus, the system of Equation (18) includes three unknowns—H, E, and A—and can be solved to yield the amounts of each of these three spectral contributors present in each particular reticulocyte, or collectively for all cells including all reticulocytes in the sample if the pixels selected for analysis collectively correspond to all of the identified cells in the images.

Nonetheless, the methods and systems disclosed herein present a simpler, more efficient method for determining amounts of reticulocyte constituents. As shown above, Equation (13)—with suitable weight coefficients—can be used to determine constituent amounts of only those constituents of interest, increasing the speed with which sample analysis can be completed. Further, in complex samples where the number of spectral contributors is not well known, it can be difficult to construct a system of equations such as in Equation (18). Equation (13), however, permits amounts of specific reticulocyte constituents to be determined even if the presence of other spectral contributors in the reticulocyte is not well established. Thus, while in some embodiments the spectral contributions from hemoglobin, eosin, and azure in the system of Equation (18) can be distinguished by obtaining images at three different illumination wavelengths, using more than three features and/or more than three illumination wavelengths as described herein to determine values of reticulocyte metrics such as reticulocyte hemoglobin, reticulocyte volume, mean reticulocyte hemoglobin, and mean reticulocyte volume permits correction for other systematic and non-systematic sources of error when measuring blood samples.

In addition to color-specific integrated optical densities and volumes, and reticulocyte area, other image features can be used to determine reticulocyte volumes and/or amounts of reticulocyte constituents. In some embodiments, for example, Equation (13) can include an extra term that corresponds to the product of a reticulocyte's perimeter and a weight coefficient. An appropriate weight coefficient can be determined for the reticulocyte perimeter term from training data, as described above. More generally, a variety of additional terms derived from reticulocyte images, with suitable weight coefficients determined from training data, can be included in Equation (13). Such terms can include geometrical image features relating to the morphology of the reticulocytes and/or color-specific measurements of integrated optical density and volume at more than three or four illumination wavelengths. Without wishing to be bound by theory, the additional terms may allow the fitting—which is performed simultaneously on reference sample information to determine values of all weighting factors—to correct for effects such as imaging aberrations, absorption from other sample components, and systemic measurement errors, that are not fully accounted for by the model of Equation (13). For example, it has been found that the inclusion of integrated optical density and reticulocyte volume terms corresponding to a red illumination wavelength and a term corresponding to reticulocyte area improves the accuracy of determination of reticulocyte hemoglobin in many samples as compared to measurement techniques that do not use sample images acquired at a red illumination wavelength or reticulocyte area measurements.

In general, the methods and systems disclosed herein can be used to determine amounts of naturally present constituents in samples (e.g., hemoglobin in reticulocytes) and/or amounts of constituents that have been added to samples (e.g., stains that have been applied, and that bind to reticulocytes). Further, in some embodiments, the methods and systems disclosed herein can be used to determine the amounts of more than one constituent present in the sample. For example, by applying suitable stains and/or selecting appropriate central wavelengths for the sample images, amounts of two or more constituents can be determined. Consider a sample that includes hemoglobin as a naturally-occurring absorbing constituent. The sample can be stained with two broadly absorptive stains S(1) and S(2), and with a third stain S(3) with a relatively narrow absorption band. S(3) selectively binds to a particular constituent of interest in reticulocytes such that measuring the amount of S(3) present yields a measurement of the constituent.

If the absorption spectra of hemoglobin and S(3) are sufficiently separated spectrally such that hemoglobin has significant absorption at only wavelengths $\lambda_1$, $\lambda_2$, and $\lambda_3$ but not at $\lambda_4$, and S(3) has significant absorption at only wavelengths $\lambda_2$, $\lambda_3$, and $\lambda_4$ but not at $\lambda_1$, then assuming S(1) and S(2) have significant absorption at all four wavelengths, the amount of reticulocyte hemoglobin can be determined according to the methods disclosed herein for measuring reticulocyte constituent amounts from images of the sample corresponding to illumination wavelengths $\lambda_1$, $\lambda_2$, and $\lambda_3$, and the amount of S(3) can be determined according to the same methods from images of the sample corresponding to illumination wavelengths $\lambda_2$, $\lambda_3$, and $\lambda_4$. These approaches can be generalized further to larger numbers of constituents of interest, and larger or smaller numbers of broadly absorptive spectral contributors such as S(1) and S(2).

Reticulocyte Results Reporting

In certain embodiments, the identified reticulocytes, determined reticulocyte volumes, constituent amounts, mean reticulocyte volume, and/or mean constituent concentrations can be displayed to a system operator using, e.g., display 110. Volume and constituent results can be displayed on a per reticulocyte basis, or as averaged results for the whole sample. Also, calculated numerical results (e.g., for individual reticulocytes) can be overlaid atop one or more images of the reticulocytes. In general, a system operator can exercise control over the manner in which results are displayed using human interface unit 112 (e.g., a keyboard and/or mouse and/or any other input device). The system operator can also exercise control over any of the other parameters, conditions, and options associated with the methods disclosed herein through interface unit 112 and display 110.

One or more metrics can also be calculated from the mean reticulocyte volume and/or mean reticulocyte hemoglobin measurements and displayed. In some embodiments, for example, reticulocyte distribution width can be calculated and displayed for a human operator. In addition, mean reticulocyte hemoglobin measurements can be used with a hematocrit value for the sample to calculate mean reticulocyte hemoglobin concentration. Additional details regarding methods and systems for displaying reticulocyte images and associated reticulocyte metrics can be found in U.S. patent application Ser. No. 13/526,223, filed on Jun. 18, 2012, the entire contents of which are incorporated herein by reference.

Reticulocyte volume and constituent concentration measurements and/or metrics calculated therefrom can be stored along with sample images in an electronic storage unit associated with control system 108. For example, this information can be stored in an electronic record associated with the patient to whom sample 104 corresponds. Alternatively, or in addition, the information can be transmitted to one or more physicians or other treatment personnel. The information can be transmitted via a network (e.g., a computer network) to a computing device. Further, the information can be transmitted to a handheld device such as a mobile phone, and the transmission can include an alert or warning if the metrics fall outside a predetermined range of values.

Methods and systems for red blood cell identification and measurement are disclosed, for example, in U.S. patent application Ser. No. 13/446,967, filed on Apr. 13, 2012, the entire contents of which are incorporated herein by reference.

Automated Sample Preparation Systems

Figure 8:
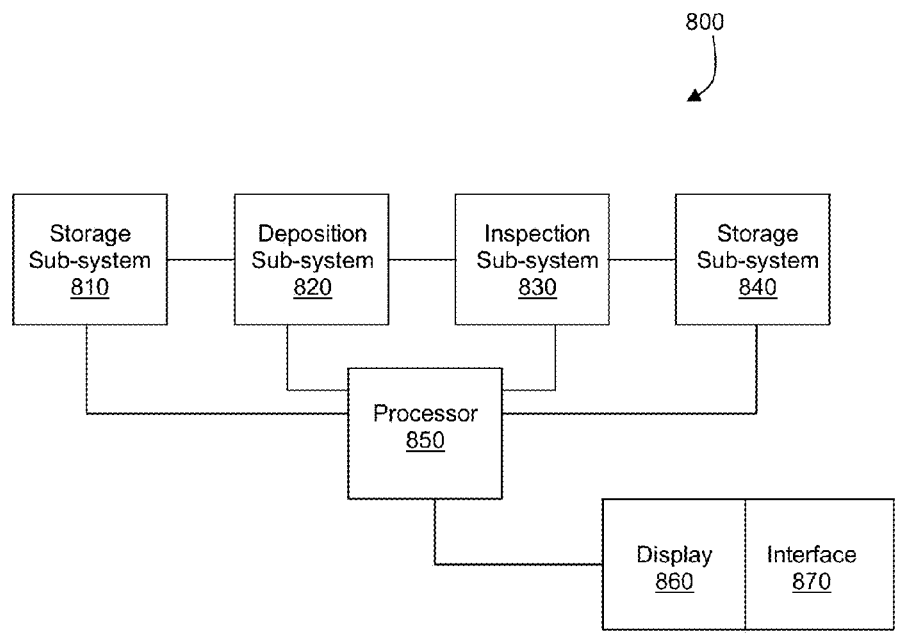
FIG. 8 is a schematic diagram of an automated sample processing system.

The systems and methods disclosed herein can be used with a variety of different automated sample preparation systems. FIG. 8 shows a schematic diagram of an embodiment of an automated sample preparation system 800. System 800 includes multiple sub-systems for storing substrates, depositing samples on substrates, inspecting samples prepared on substrates, and storing prepared samples.

Substrate storage sub-system 810 is configured to store substrates prior to the deposition of samples thereon. Substrates can include, for example, microscope slides, coverslips, and similar planar, optically transparent substrates. The substrates can be formed from a variety of different amorphous or crystalline materials including various types of glasses. Sub-system 810 can include a manipulator that selects individual substrates from a storage container and transfers the selected substrates to sample deposition sub-system 820.

Sample deposition sub-system 820 deposits a selected quantity of a sample of interest—such as a blood sample—onto a substrate. Sub-system 820 includes, in general, a variety of fluid transfer components (e.g., pumps, fluid tubes, valves) configured to deposit the sample. The fluid transfer components can also be configured to expose the substrate to solutions of various types, including rinse solutions, one or more stains that bind to the sample, fixing solutions, and/or buffer solutions. Sub-system 820 can also feature fluid removal components (e.g., a vacuum sub-system) and a drying apparatus to ensure that the sample is fixed to the substrate. A substrate manipulator can transfer the substrate supporting the sample to imaging sub-system 830.

Inspection sub-system 830 includes various components for obtaining images of samples on substrates, and for analyzing the images to determine information about the samples. For example, inspection sub-system 830 can include one or more light sources (e.g., light emitting diodes, laser diodes, and/or lasers) for directing incident light to a sample. Imaging sub-system 830 can also include an optical apparatus (e.g., a microscope objective) for capturing transmitted and/or reflected light from a sample. A detector (e.g., a CCD detector) coupled to the optical apparatus can be configured to capture images of the sample. Information derived from analysis of the images of the sample can be stored on a variety of optical and/or electronic storage media for later retrieval and/or further analysis.

Following inspection, a substrate manipulator can transfer the substrate to storage sub-system 840. Storage sub-system 840 can label individual substrates, for example, with information relating to the source of the sample applied to the substrate, the time of analysis, and/or any irregularities identified during analysis. Storage sub-system can also store processed substrates in multi-substrate racks, which can be removed from system 800 as they are filled with substrates.

As shown in FIG. 8, each of the various sub-systems of system 800 can be linked to a common electronic processor 850. Processor 850 can be configured to control the operation of each of the sub-systems of system 800 in automated fashion, with relatively little (or no) input from a system operator. Results from the analysis of samples can be displayed on system display 860 for a supervising operator. Interface 870 permits the operator to issue commands to system 800 and to manually review the automated analysis results.

Additional aspects and features of automated sample processing systems are disclosed, for example, in U.S. patent application Ser. No. 13/293,050, filed on Nov. 9, 2011, the entire contents of which are incorporated herein by reference.

Hardware and Software Implementation

The method steps and procedures described herein can be implemented in hardware or in software, or in a combination of both. In particular, electronic processor 114 can include software and/or hardware instructions to perform any of the methods discussed above. The methods can be implemented in computer programs using standard programming techniques following the method steps and figures disclosed herein. Program code is applied to input data to perform the functions described herein. The output information is applied to one or more output devices such as a printer, or a display device, or a web page on a computer monitor with access to a website, e.g., for remote monitoring.

Each program is preferably implemented in a high level procedural or object oriented programming language to communicate with a processor. However, the programs can be implemented in assembly or machine language, if desired. In any case, the language can be a compiled or interpreted language. Each computer program can be stored on a storage medium or device (e.g., an electronic memory) readable by the processor, for configuring and operating the processor to perform the procedures described herein.

Figure 9:
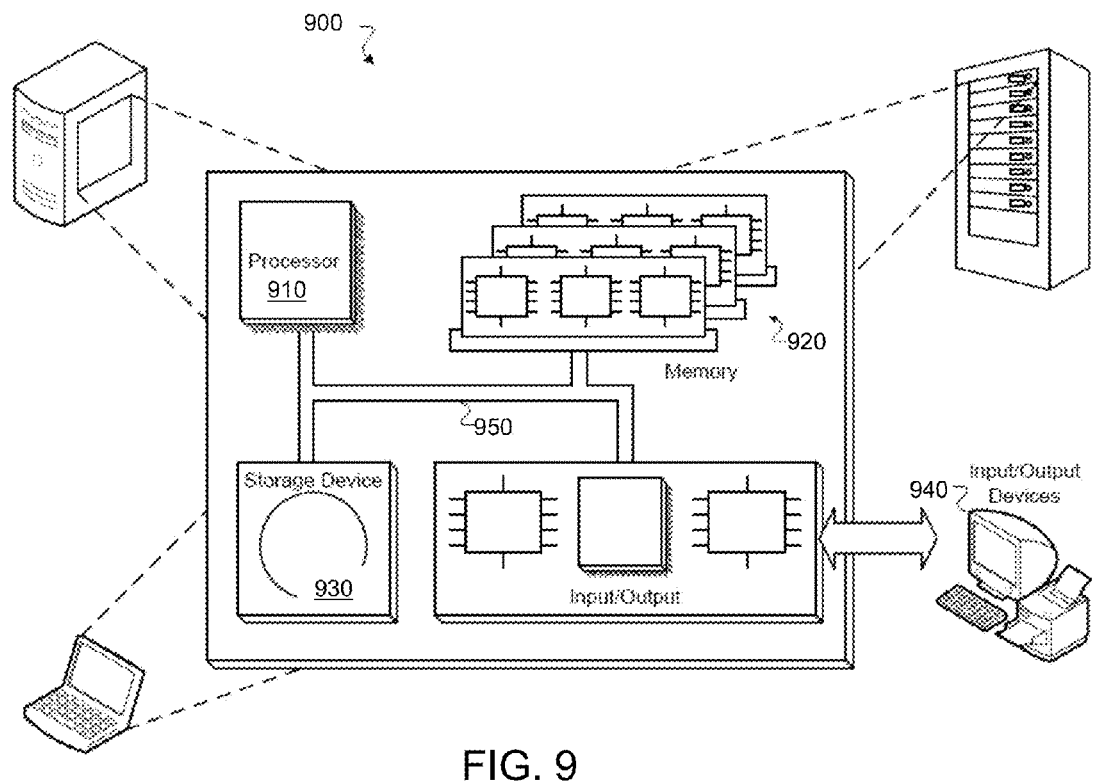
FIG. 9 is a schematic diagram of a computing system for measuring volume, constituents, and other features of reticulocytes.

FIG. 9 is a schematic diagram of a computer system 900 that can be used to control the operations described in association with any of the computer-implemented methods described herein, according to one embodiment. The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. In one embodiment, the processor 910 is a single-threaded processor. In another embodiment, the processor 910 is a multi-threaded processor. The processor 910 is capable of processing instructions stored in the memory 920 or on the storage device 930 to display graphical information for a user interface on the input/output device 940. The processor 910 can be substantially similar to the processor 850 described above with reference to FIG. 8.

The memory 920 stores information within the system 900. In some embodiments, the memory 920 is a computer-readable medium. The memory 920 can include volatile memory and/or non-volatile memory.

The storage device 930 is capable of providing mass storage for the system 900. In general, the storage device 930 can include any non-transitory tangible media configured to store computer readable instructions. In one embodiment, the storage device 930 is a computer-readable medium. In various different embodiments, the storage device 930 may be a floppy disk device, a hard disk device, an optical disk device, or a tape device.

The input/output device 940 provides input/output operations for the system 900. In some embodiments, the input/output device 940 includes a keyboard and/or pointing device. In some embodiments, the input/output device 940 includes a display unit for displaying graphical user interfaces. In some embodiments, the input/output device 940 includes one or more of the display 860 and interface 870 described above with reference to FIG. 8.

The features described can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described embodiments by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Various software architectures can be used for implementing the methods and systems described in this application. For example, a publish/subscribe messaging pattern can be used in implementing the methods and systems described herein. In the case of publish/subscribe messaging, the system includes several hardware and software modules that communicate only via a messaging module. Each module can be configured to perform a specific function. For example, the system can include one or more of a hardware module, a camera module, and a focus module. The hardware module can send commands to the imaging hardware implementing auto-focus functions, which in turn triggers a camera to acquire images. In some embodiments, the hardware module can include the control system 108 described above with reference to FIG. 1.

A camera module can receive images from the camera and determine camera parameters such as shutter time or focus. Images can also be buffered in the computer's memory before being processed by the camera module. When performing the initial search for the tilt of the slide, the camera module can also send a message interrupting the hardware module when it has seen enough images to determine the proper shutter time or focus. In some embodiments, the camera module includes the detector 106 described above with reference to FIG. 1.

The system can also include a focus module that can be implemented as software, hardware or a combination of software and hardware. In some embodiments, the focus module examines all the frames in a stack and estimates how far the stack is from the ideal or ideal focal distance. The focus module can also be responsible for assigning a focus score to each frame in a stack of images.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Alternatively, the computer can have no keyboard, mouse, or monitor attached and can be controlled remotely by another computer The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 910 carries out instructions related to a computer program. The processor 910 can include hardware such as logic gates, adders, multipliers and counters. The processor 910 can further include a separate arithmetic logic unit (ALU) that performs arithmetic and logical operations.

Other Embodiments

It is to be understood that the foregoing description is intended to illustrate and not limit the scope of the disclosure, which is defined by the scope of the appended claims. Other aspects, advantages, and modifications are within the scope of the following claims. For example, although the foregoing description and the schematic diagram in FIG. 1 discuss the measurement of transmitted light from a sample, the methods and systems disclosed herein can also be used when images of the sample correspond to light reflected from the sample. Certain samples may be naturally reflective, or can be tagged with reflective markers, such that reflected light provides a convenient method for determining amounts of cellular constituents and/or volume. In some embodiments, sample 104 can be positioned atop a substrate such as a microscope slide with a reflective coating. The reflective coating can function to direct once-transmitted light back through the sample a second time, so that the measured "reflected" light actually corresponds to incident light that has twice been transmitted through the sample.

In general, the methods and systems disclosed herein can be used to determine reticulocyte counts, per-reticulocyte volumes, constituent contents, and/or sample mean reticulocyte volume or mean reticulocyte constituents for a variety of different sample types. For example, reticulocyte volumes and constituents such as hemoglobin or other proteins can be determined for samples that include reticulocytes from body fluids and tissues, including blood, bone marrow, urine, epithelial tissue, tumors, semen, spittle, and other tissues or circulating or non-circulating biological fluids.

What is claimed is:

1. A method for identifying reticulocytes in a blood sample deposited on a substrate, the method comprising:
    illuminating the sample with incident light at two different wavelengths, obtaining a two-dimensional image of the sample corresponding to a first one of the wavelengths, and obtaining a two-dimensional image of the sample corresponding to a second one of the wavelengths;
    analyzing the images to identify a set of representative red blood cells;
    determining an area of each of the red blood cells in the set;
    determining a color value of each of the red blood cells in the set; and
    for each one of the red blood cells in the set, identifying the red blood cell as a reticulocyte if the area of the red blood cell exceeds an area cutoff value and the color value of the red blood cell is less than a color cutoff value,
    wherein the color value of each one of the red blood cells comprises a difference between optical density values of the red blood cell at the two illumination wavelengths.

2. The method of claim 1, wherein one of the wavelengths is between 400 nm and 475 nm, and the other wavelength is between 575 nm and 600 nm.

3. The method of claim 1, wherein determining the color value of each of the identified red blood cells comprises, for each one of the red blood cells:
    determining a set of pixels associated with the cell;
    determining optical densities corresponding to the first wavelength for each one of the set of pixels;
    determining optical densities corresponding to the second wavelength for each one of the set of pixels;
    determining a mean optical density corresponding to the first wavelength for the set of pixels;
    determining a mean optical density corresponding to the second wavelength for the set of pixels; and
    calculating a difference between the mean optical densities to determine the color value of the cell.

4. The method of claim 1, wherein determining the area of each of the red blood cells in the set comprises, for each one of the red blood cells:
    determining a set of pixels associated with the cell; and
    determining the area of the cell by counting the number of pixels in the set.

5. The method of claim 1, wherein determining the area of each of the red blood cells in the set comprises, for each one of the red blood cells:
    determining a set of pixels associated with the cell;
    determining a polygon that circumscribes the set of pixels; and
    determining the area of the cell by calculating an area of the polygon.

6. The method of claim 1, wherein the color cutoff value is based on a percentile of a distribution of the color values of the red blood cells.

7. The method of claim 6, wherein the percentile corresponds to a 70th percentile within the distribution of color values of the red blood cells.

8. The method of claim 6, wherein the color cutoff value corresponds to a sum of the percentile and a color offset value.

9. The method of claim 8, further comprising determining the percentile and the color offset value based on a set of training data in which the numbers of reticulocytes are known.

10. The method of claim 1, wherein the area cutoff value is based on a percentile of a distribution of the areas of the red blood cells.

11. The method of claim 10, wherein the percentile corresponds to a 20th percentile of the distribution of areas of the red blood cells.

12. The method of claim 10, wherein the area cutoff value corresponds to a sum of the percentile and an area offset value.

13. The method of claim 12, further comprising determining the percentile and the area offset value based on a set of training data in which the numbers of reticulocytes are known.

14. The method of claim 1, further comprising excluding the red blood cell from the representative set if a standard deviation of optical densities of pixels associated with the red blood cell at one of the two wavelengths is larger than a cutoff value.

15. The method of claim 1, further comprising excluding the red blood cell from the representative set if a standard deviation of optical densities of pixels associated with the red blood cell at a wavelength different from the two wavelengths is larger than a cutoff value.

16. The method of claim 1, further comprising, for each of the red blood cells identified as reticulocytes, determining a volume of the reticulocyte.

17. The method of claim 16, further comprising determining the volume of the reticulocyte based on integrated optical densities of the reticulocyte corresponding to multiple illumination wavelengths.

18. The method of claim 17, further comprising determining a mean reticulocyte volume parameter for the sample.

19. The method of claim 1, further comprising, for each of the red blood cells identified as reticulocytes, determining a hemoglobin content of the reticulocyte.

20. The method of claim 19, further comprising determining the hemoglobin content of the reticulocyte based on a weighted combination of an area of the reticulocyte, volumes of the reticulocyte corresponding to multiple illumination wavelengths, and integrated optical densities of the reticulocyte corresponding to the multiple illumination wavelengths.

21. The method of claim 19, further comprising determining a mean reticulocyte hemoglobin value for the sample.

22. A system for identifying reticulocytes in a blood sample deposited on a substrate, the system comprising:
a source configured to illuminate the sample with incident light at two different wavelengths;
a detector configured to obtain a two-dimensional image of the sample corresponding to a first one of the wavelengths, and to obtain a two-dimensional image of the sample corresponding to a second one of the wavelengths; and
an electronic processor configured to:
analyze the images to identify a set of representative red blood cells;
determine an area of each of the red blood cells in the set;
determine a color value of each of the red blood cells in the set;
for each one of the red blood cells in the set, identify the red blood cell as a reticulocyte if the area of the red blood cell exceeds an area cutoff value and the color value of the red blood cell is less than a color cutoff value,
wherein the electronic processor is configured to determine the color value of each one of the red blood cells based on a difference between optical density values of the red blood cell at the two illumination wavelengths.

23. The system of claim 22, wherein the first wavelength is between 400 nm and 475 nm, and the second wavelength is between 575 nm and 600 nm.

24. The system of claim 22, wherein for each one of the red blood cells in the set, the electronic processor is configured to determine the color value of the cell by:
determining a set of pixels associated with the cell;
determining optical densities corresponding to the first wavelength for each one of the set of pixels;
determining optical densities corresponding to the second wavelength for each one of the set of pixels;
determining a mean optical density corresponding to the first wavelength for the set of pixels;
determining a mean optical density corresponding to the second wavelength for the set of pixels; and
calculating a difference between the mean optical densities to determine the color value of the cell.

25. The system of claim 22, wherein for each one of the red blood cells in the set, the electronic processor is configured to determine the area of the cell by:
determining a set of pixels associated with the cell; and
determining the area of the cell by counting the number of pixels in the set.

26. The system of claim 22, wherein for each one of the red blood cells, the electronic processor is configured to determine the area of the cell by:
determining a set of pixels associated with the cell;
determining a polygon that circumscribes the set of pixels; and
determining the area of the cell by calculating an area of the polygon.

27. The system of claim 22, wherein electronic processor is configured to determine the color cutoff value based on a percentile of a distribution of the color values of the red blood cells.

28. The system of claim 27, wherein the percentile corresponds to a 70th percentile within the distribution of color values of the red blood cells.

29. The system of claim 27, wherein electronic processor is configured to determine the color cutoff value as a sum of the percentile and a color offset value.

30. The system of claim 29, wherein the electronic processor is configured to determine the percentile and the color offset value based on a set of training data in which the numbers of reticulocytes are known.

31. The system of claim 22, wherein the electronic processor is configured to determine the area cutoff value based on a percentile of a distribution of the areas of the red blood cells.

32. The system of claim 31, wherein the percentile corresponds to a 20th percentile of the distribution of areas of the red blood cells.

33. The system of claim 31, wherein the electronic processor is configured to determine the area cutoff value as a sum of the percentile and an area offset value.

34. The system of claim 33, wherein the electronic processor is configured to determine the percentile and the area offset value based on a set of training data in which the numbers of reticulocytes are known.

35. The system of claim 22, wherein the electronic processor is configured to exclude the red blood cell from the representative set if a standard deviation of optical densities of pixels associated with the red blood cell at one of the two wavelengths is larger than a cutoff value.

36. The system of claim 22, wherein the electronic processor is configured to exclude the red blood cell from the representative set if a standard deviation of optical densities of pixels associated with the red blood cell at a wavelength different from the two wavelengths is larger than a cutoff value.

37. The system of claim 22, wherein for each of the red blood cells identified as reticulocytes, the electronic processor is configured to determine volumes of the reticulocyte corresponding to the two different wavelengths.

38. The system of claim 37, wherein the electronic processor is configured to determine the volumes of the reticulocyte based on integrated optical densities of the reticulocyte corresponding to the two different wavelengths.

39. The system of claim 38, wherein the electronic processor is configured to determine a mean reticulocyte volume parameter for the sample.

40. The system of claim 22, wherein for each of the red blood cells identified as reticulocytes, the electronic processor is configured to determine a hemoglobin content of the reticulocyte.

41. The system of claim 40, wherein the electronic processor is configured to determine the hemoglobin content of the reticulocyte based on a weighted combination of an area of the reticulocyte, volumes of the reticulocyte corresponding to multiple illumination wavelengths, and integrated optical densities of the reticulocyte corresponding to the multiple illumination wavelengths.

42. The system of claim 40, wherein the electronic processor is configured to determine a mean reticulocyte hemoglobin value for the sample.

* * * * *